(12) United States Patent
Juo et al.

(10) Patent No.: US 8,716,256 B2
(45) Date of Patent: May 6, 2014

(54) METHOD OF THERAPY AND DIAGNOSIS OF ATHEROSCLEROSIS

(75) Inventors: Suh-Hang Juo, Kaohsiung (TW);
Ku-Chung Chen, Kaohsiung (TW);
I-Chung Hsieh, Kaohsiung (TW);
Ching-Yu Hu, Kaohsiung (TW)

(73) Assignee: Kaoshiung Medical University, Kaohsiung (TW)

( * ) Notice: Subject to any disclaimer, the term of this patent is extended or adjusted under 35 U.S.C. 154(b) by 187 days.

(21) Appl. No.: 13/152,520

(22) Filed: Jun. 3, 2011

(65) Prior Publication Data
US 2012/0252867 A1    Oct. 4, 2012

(30) Foreign Application Priority Data

Apr. 1, 2011  (TW) .............................. 100111567 A

(51) Int. Cl.
| | | |
|---|---|---|
| A61K 31/70 | (2006.01) | |
| C07H 21/02 | (2006.01) | |
| C07H 21/04 | (2006.01) | |
| C12N 5/00 | (2006.01) | |
| C12Q 1/68 | (2006.01) | |

(52) U.S. Cl.
USPC ...... 514/44 A; 514/44 R; 536/23.1; 536/24.1; 536/24.5

(58) Field of Classification Search
None
See application file for complete search history.

(56) References Cited

U.S. PATENT DOCUMENTS

| | | |
|---|---|---|
| 6,900,241 B2 | 5/2005 | Romanczyk, Jr. et al. |
| 7,415,360 B2 | 8/2008 | Wang |
| 7,893,034 B2 | 2/2011 | Slack et al. |
| 7,919,245 B2 | 4/2011 | Brown et al. |
| 2009/0220589 A1* | 9/2009 | Trieu et al. .................... 424/450 |

FOREIGN PATENT DOCUMENTS

WO    WO 2010/135570 A1    11/2010

OTHER PUBLICATIONS

Chen et al., Journal of Cell Science vol. 124:4115-4124, 2011.*
Reid et al., "Circulating MicroRNAs: Association with Disease and Potential Use as Biomarkers," Crit. Rev. Oncol/Hematol, vol. 80, pp. 193-208 (2010).

* cited by examiner

*Primary Examiner* — Sean McGarry
(74) *Attorney, Agent, or Firm* — Muncy, Geissler, Olds & Lowe, P.C.

(57) ABSTRACT

There is provided a method of therapy of atherosclerosis, by providing microRNA let-7g, an analogue thereof or modified let-7g to organisms to inhibit the expression of lectin-like oxidized low density lipoprotein receptor-1 (LOX-1), and the binding of LOX-1 and oxidized low-density lipoprotein (ox-LDL), so as to block the pathogenesis of atherosclerosis. Also, a method of diagnosis of atherosclerosis comprises determining the levels of microRNA let-7g in serum or plasma samples of organisms, in which the levels of microRNA let-7g is estimated in individuals with atherosclerosis as compared to individuals without atherosclerosis.

1 Claim, 19 Drawing Sheets

-1500 GCCTGCATGT CTCGAGATAA ATCCTAAGTT AACAGATTGT CTTGGTAACT
-1451 GAACTGTAAC ACTTATTTTC ATGTTAGAAT TCTTTAATTT TTTAATTTTG
               OCT-1
-1401 TTTATTTTCT TTTGTTTGTC TGTTTTTATT TTTTGAGACA GAGTCTCACT
-1351 CTGTTGCCTA GGCTGGAGTG CAGTGGCGCG ATCTCAGCTC GCTGCAACCT
-1301 CCGCCTCCCG GGTTCAAGTA ATTCTCCTGC CTCAGCCTCC CAGGTAGCTG
-1251 GGACTACAGG TGCATGCCAC CATGCCTGGC TAATTTTTTG TATTTTTAGT
-1201 AGAGACAGGG TTTCACCATG TTAGCCAGGA TGGGTCTTGA TCTCCTGACC
                                 GATA-1
-1151 TTGTAAGCCA CCGTGCCCGG CCTATTCTTT ATTCTTTTGA GACAGAGTCC
-1101 TGCTCTTGTT GCCCAGGCTG GAGTGCAATG GTGCAATCTC GGCTCACTGC
                                           C/EBPb
-1051 AATCTCAGCC TCCTGGGTTC AAGCGATGCT CTTGCCTCAG CCTCCCAAGT

FIG. 15

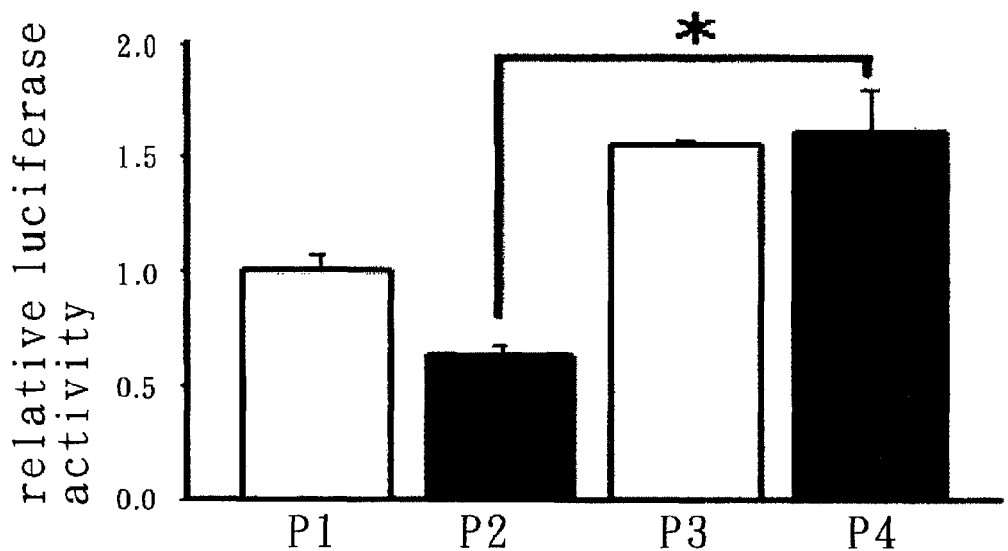

FIG. 16

SEQUENCE LISTING

<160> NUMBER OF SEQ ID NOS: 23

<210> SEQ ID NO 1
<211> LENGTH: 84
<212> TYPE: RNA
<213> ORGANISM: Homo sapiens

<400> SEQUENCE: 1
aggcugaggu aguaguuugu acaguuugag ggucuaugau accacccggu acaggagaua     60
acuguacagg ccacugccuu gcca                                            84

<210> SEQ ID NO 2
<211> LENGTH: 22
<212> TYPE: RNA
<213> ORGANISM: Homo sapiens

<400> SEQUENCE: 2
ugagguagua guuuguacag uu                                              22

<210> SEQ ID NO 3
<211> LENGTH: 20
<212> TYPE: DNA
<213> ORGANISM: Artificial Sequence
<220> FEATURE:
<223> OTHER INFORMATION: primer for real time PCR

<400> SEQUENCE: 3
ttactctcca tggtggtgcc                                                 20

<210> SEQ ID NO 4
<211> LENGTH: 20
<212> TYPE: DNA
<213> ORGANISM: Artificial Sequence
<220> FEATURE:
<223> OTHER INFORMATION: primer for real time PCR

<400> SEQUENCE: 4
agcttcttct gcttgttgcc                                                 20

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
aaaggatcca tgactttga tgacc                                            25

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
aaatctagat cactgtgctc ttaggtttg                                       29

<210> SEQ ID NO 7
<211> LENGTH: 18
<212> TYPE: DNA
<213> ORGANISM: Artificial Sequence
<220> FEATURE:

<223> OTHER INFORMATION: primer for real time PCR

<400> SEQUENCE: 7
gtgaaggtcg gagtcaac                                                    18

<210> SEQ ID NO 8
<211> LENGTH: 18
<212> TYPE: DNA
<213> ORGANISM: Artificial Sequence
<220> FEATURE:
<223> OTHER INFORMATION: primer for real time PCR

<400> SEQUENCE: 8
gttgaggtca atgaaggg                                                    18

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
caaactagta tttgaaggct ctggaagaa                                        29

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
taaacgcgta cacaaatgtt cacagca                                          27

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
aactcagtct tcttcgttct gttatcacct tcccc                                 35

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
ggggaaggtg ataacagaac gaagaagact gagtt                                 35

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
caaacgcgtg cctgcatgtc tcgagataa                                        29

<210> SEQ ID NO 14

```
<211> LENGTH: 29
<212> TYPE: DNA
<213> ORGANISM: Artificial Sequence
<220> FEATURE:
<223> OTHER INFORMATION: primer

<400> SEQUENCE: 14
taaaagatta atcaggcaaa aggaaacgg                                    29

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15
caaacgcgta gctggtatta caggtgcc                                     28

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16
caaacgcgtc agagcgaggc tccatct                                      27

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
ctgaactgta acacttgggg gcatgttaga attctttaa                         39

<210> SEQ ID NO 18
<211> LENGTH: 39
<212> TYPE: DNA
<213> ORGANISM: Artificial Sequence
<220> FEATURE:
<223> OTHER INFORMATION: primer

<400> SEQUENCE: 18
ttaaagaatt ctaacatgcc cccaagtgtt acagttcag                         39

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
ccctgtctca gcccatacag a                                            21

<210> SEQ ID NO 20
<211> LENGTH: 21
<212> TYPE: DNA
<213> ORGANISM: Artificial Sequence
<220> FEATURE:
<223> OTHER INFORMATION: primer for real time PCR

<400> SEQUENCE: 20
```

```
gctgcaaatt ggtggttgga t                                              21

<210> SEQ ID NO 21
<211> LENGTH: 20
<212> TYPE: DNA
<213> ORGANISM: Artificial Sequence
<220> FEATURE:
<223> OTHER INFORMATION: primer for real time PCR

<400> SEQUENCE: 21
tgaccacagt ccatgccatc                                                20

<210> SEQ ID NO 22
<211> LENGTH: 20
<212> TYPE: DNA
<213> ORGANISM: Artificial Sequence
<220> FEATURE:
<223> OTHER INFORMATION: primer for real time PCR

<400> SEQUENCE: 22
gacggacaca ttggggtag                                                 20

<210> SEQ ID NO 23
<211> LENGTH: 500
<212> TYPE: DNA
<213> ORGANISM: Homo sapiens
<220> FEATURE:
<223> OTHER INFORMATION: 1001th to 1500th upstream region of let-7g
      promoter

<400> SEQUENCE: 23
gcctgcatgt ctcgagataa atcctaagtt aacagattgt gttggtaact gaactgtaac     60
acttattttc atgttagaat tctttaattt tttaattttg tttattttct tttgtttgtc    120
tgttttattt ttttgagaca gagtctcact ctgttgccta ggctggagtg cagtggcgcg    180
atctcagctc gctgcaacct ccgcctcccg ggttcaagta attctcctgc ctcagcctcc    240
caggtagctg ggactacagg tgcatgccac catgcctggc taatttttg tatttttagt     300 agagacaggg tttcaccatg ttagccagga tgggtcttga tctcctgacc ttgtaagcca    360
ccgtgcccgg cctattcttt attcttttga dacagagtcc tgctcttgtt gcccaggctg    420
gagtgcaatg gtgcaatctc ggctcactgc aatctcagcc tcctgggttc aagcgatgct    480
cttgcctcag cctcccaagt                                               500
```

METHOD OF THERAPY AND DIAGNOSIS OF ATHEROSCLEROSIS

BACKGROUND OF THE INVENTION

1. Field of the Invention

The present invention relates to a method of therapy and diagnosis of atherosclerosis, particularly to a method of therapy and diagnosis of atherosclerosis based on the relationship between microRNA let-7g and lectin-like oxidized low-density lipoprotein (LOX-1).

2. Description of the Related Art

Cardiovascular diseases, generally referring to diseases, disorders and conditions involved in the cardiovascular system, is a common issue to people in developed countries. It is believed that the pathogenesis of atherosclerosis plays an important role in cardiovascular diseases.

Atherosclerosis is characterized by chronic inflammation, and lipid-rich plaques in blood vessel walls. Generally, the accumulation of oxidized low-density lipoprotein (oxLDL) in vessel walls stimulates the production of various proinflammatory mediators, such as IL-8 and MCP-1, leads to inflammatory, proliferation and migration of aortic smooth muscle cells, and finally affects the circulation of blood to result in multiple diseases.

It has been reported that a scavenger receptor, also known as lectin-like oxidized low-density lipoprotein receptor-1 (LOX-1), plays a significant role in the pathogenesis of atherosclerosis, and which can bind with oxLDL and mediate the internalization, as well as the pathological changes of oxLDL in blood vessel walls. However, the detailed mechanism and relationship between oxLDL and LOX-1 has not been fully understood yet. As a result, conventional therapies of atherosclerosis only can avoid the aggravation of atherosclerosis by providing either appropriate medications or basic lifestyle change, for example low-fat diet, to reduce high level of cholesterol or lipoprotein. Nevertheless, it is still lack of a directly and effectively therapeutic strategy to improve the proliferation and migration of vascular smooth muscle cells.

On the other hand, conventional diagnosis of atherosclerosis generally based on patients' history, blood pressure and the physical properties of arteries. They are mainly identified by measuring the flexibility or diameter of arterial vessels walls by using supersonic diagnostic set or phonocardiograph. However, the conventional diagnosis of atherosclerosis has problem in specifically detecting atherosclerosis at early stage.

Hence, there is a pressing need of providing a new strategy of therapy and diagnosis of atherosclerosis, for the sake of rapidly and specifically identifying people at high risk of atherosclerosis, significantly improving atherosclerosis, and finally reducing the incidence to stroke, hypertension, and myocardial infarction.

MicroRNAs, being a novel class of endogenous, small and non-coding RNAs, are widely found in organisms and generally control gene expression thereof. Precisely, microRNAs will specifically target to particular genes and bind to their 3' UTR region for up-regulating or down-regulating the gene expression of the particular genes. To date, microRNA let-7 has nine family members in human beings, and plays a crucial role in cell proliferation, and cancer, wherein the pivotal role of microRNA let-7g in the regulation of Ras gene and liver cancer has been well-studied. MicroRNA-let7g is generally found in cells in the form of pre-le7g as SEQ ID NO. 1, and which is further processed of enzymatic digestion to obtain a mature form of microRNA-let7g, as set forth in SEQ ID NO. 2. Recently, microRNA let-7g is used as a new therapy of cancer, and has been put to use in developing cancer related medication or treatment.

SUMMARY OF THE INVENTION

The primary objective of this invention is to provide a method of therapy of atherosclerosis, which can down-regulate the expression of lectin-like oxidized low density lipoprotein receptor-1 (LOX-1), inhibit the binding of LOX-1 and oxidized lower-density lipoprotein (oxLDL), and also improve the proliferation and migration caused by over-expression of oxLDL, according to the relationship between microRNA let-7g, LOX-1 and transcription factor OCT-1.

The secondary objective of this invention is to provide an active substance of medication for atherosclerosis, which can block the pathogenesis of atherosclerosis so as to prevent from atherosclerotic diseases.

Another objective of this invention is to provide a method of diagnosis of atherosclerosis, which can meet a need of rapid, sensitive and specific diagnostic assay of atherosclerosis so as to facilitate the clinical evaluation of atherosclerotic patients.

Another objective of this invention is to provide a biomarker of atherosclerosis, which is specific and sensitive in determining people at high risk of atherosclerosis.

A method of therapy of atherosclerosis, by providing microRNA let-7g, an analogue thereof or modified let-7g to organisms to inhibit the expression of lectin-like oxidized low density lipoprotein receptor-1 (LOX-1), as well as the binding of lectin-like oxidized low density lipoprotein receptor-1 and oxidized low-density lipoprotein (oxLDL)

An active substance of medication for atherosclerosis comprises microRNA let-7g, an analogue thereof, or modified let-7g.

A method of diagnosis of atherosclerosis comprises determining the levels of microRNA let-7g in serum or plasma samples of organisms, in which the levels of microRNA let-7g is estimated in individuals with atherosclerosis as compared to individuals without atherosclerosis.

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 15 is an analysis data of TFSEARCH software illustrating the binding site of transcription factors of SEQ ID NO 23;

FIG. 16 is a bar chart illustrating the luciferase activity of each group;

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

Figure 1:
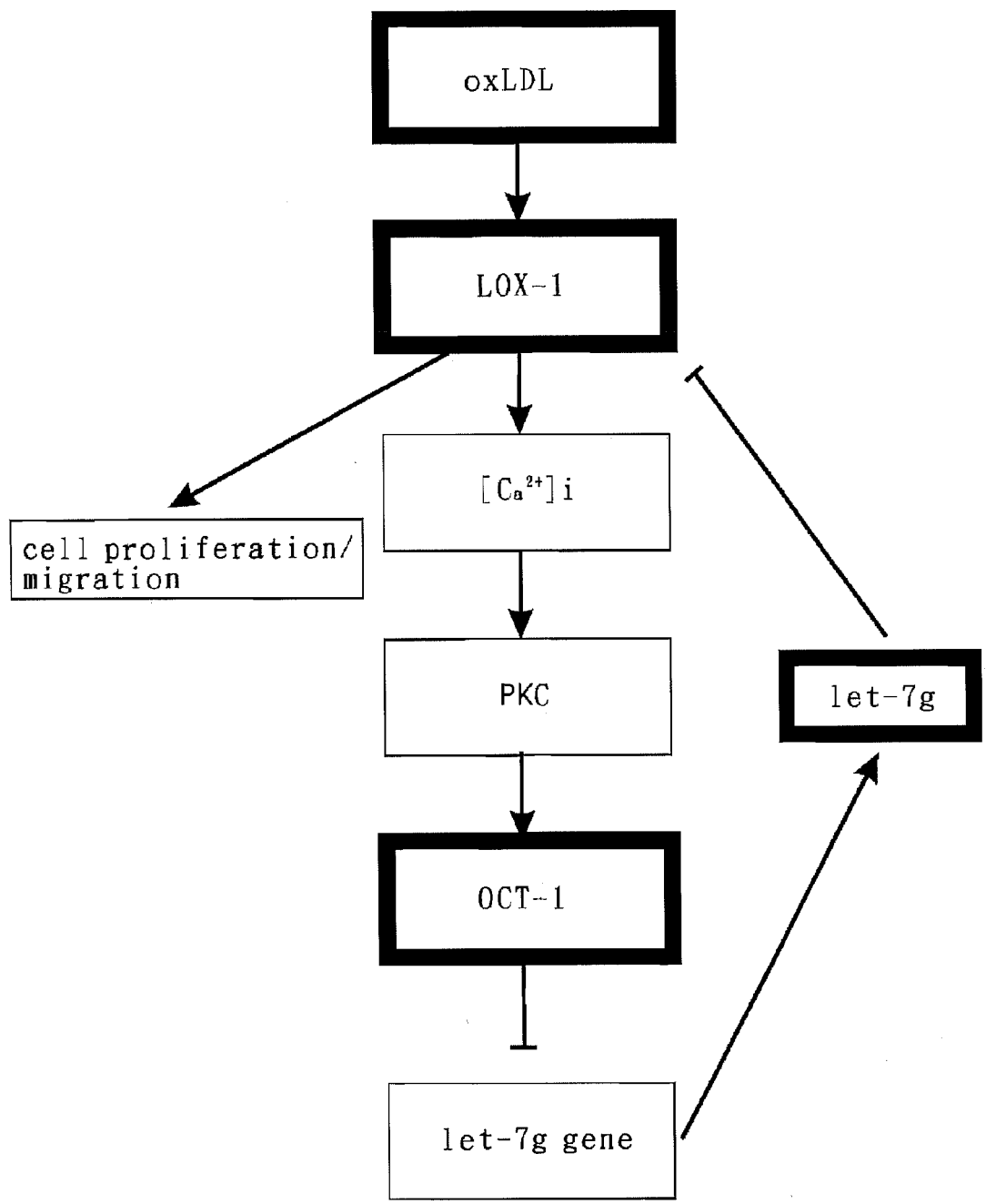
FIG. 1 is a diagram illustrating a feedback relationship between microRNA let-7g, transcription factor OCT-1, oxLDL and receptor LOX-1.

The present invention relates to a method of therapy and diagnosis of atherosclerosis, mainly based on the relationship between microRNA let-7g, transcription factor OCT-1, lectin-like oxidized low-density lipoprotein (LOX-1) and oxidized low-density lipoprotein (oxLDL) as summarized in FIG. 1, in which the microRNA let-7g is used either as an inhibitor of LOX-1, or as a diagnostic biomarker of atherosclerosis, in order to down-regulate the expression of LOX-1 for effectively inhibiting the proliferation and migration of vascular smooth muscle cells, and also to rapidly and specifically identified people at high risk of atherosclerosis.

Referring to FIG. 1, the role of microRNA let-7g in oxLDL-induced atherosclerosis and a signal transduction thereof are shown. It is note that oxLDL binds to receptor LOX-1, and provokes the $[Ca^{2+}]_i$/PKC/OCT-1/let-7g signal transduction, so that both of the genetic expression and functions of let-7g are suppressed. Precisely, transcription factor OCT-1 will bind to the promoter of let-7g gene and inhibit the gene expression of let-7g. On the contrary, let-7g will bind to the 3'UTR region of LOX-1, interfere with the binding of LOX-1 and oxLDL, and reduce the proliferation and migration of smooth muscle cells. In the following paragraphs of the present invention, the feedback relationship between oxLDL, LOX-1 and transcription factor OCT-1 of FIG. 1 is demonstrated and proved.

Figure 2:
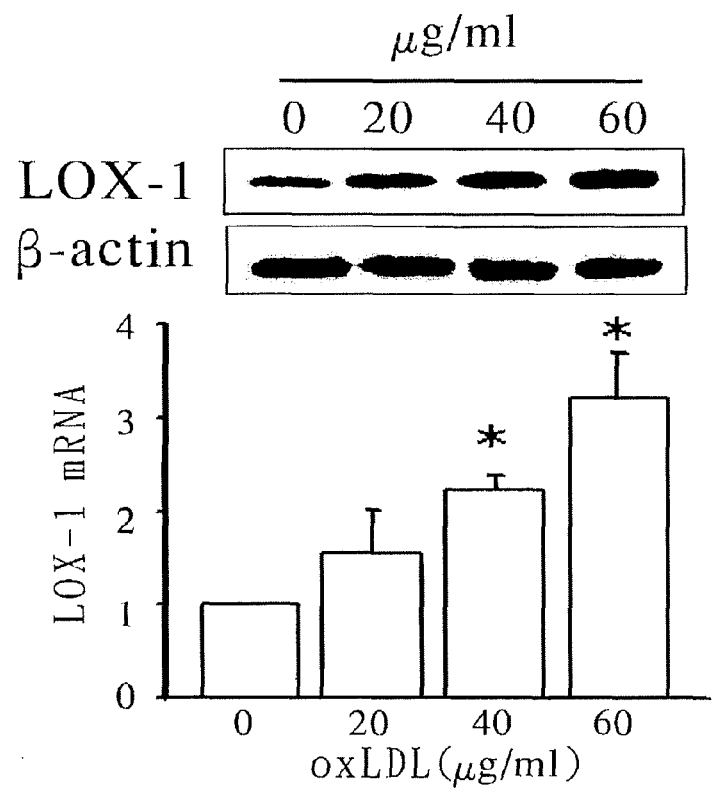
FIG. 2 is a bar chart and a western blot data illustrating the expression of LOX-1 under various levels of oxLDL.

With reference to FIG. 2, there center on the expression of oxLDL and LOX-1 in human aortic smooth muscle cells. In the present embodiment, a primary human aortic smooth muscle cells (HASMC) cell line purchased from Cascade Biologics (OR, USA) is prepared and treated with various levels of oxLDL. More specifically, the HASMC cell line is incubated in a commercial smooth muscle cell growth supplement (SMGS) medium (Cascade Biologics, OR, USA) at 37° C. in a humidified atmosphere of 95% air and 5% $CO_2$.

In the present embodiment, the HASMC cell line is grown in a 6-well plate till at a density of $2\times10^5$ cell/well, and then randomly assigned into four groups. The four groups of HASMC are co-cultured with 0, 20, 40, and 60 μg/ml of oxLDL individually for 24 hours, followed by analyzing the gene expression of HASMC via real time polymerase chain reaction (PCR) and western blot. Total RNA samples of the four groups of HASMC are prepared by using a Trizol® reagent (Invitrogen, CA, USA), and further quantitatively confirmed by a spectrophotometer at A260/A280 readings. Then, cDNA samples of the four groups of HASMC are synthesized by using a random primer and a MultiScribe™ Reverse Transcriptase Kit (Applied Biosystems Inc, CA, USA). The cDNA samples of the four groups of HASMC are sequentially diluted in 2×SYBR Green PCR Master Mix (Applied Biosystems Inc, CA, USA) to carry out quantitative real time PCR analysis. In the present invention, a primer pair of LOX-1 is designed and used in the real time PCR analysis, wherein the primer pair of LOX-1 is set forth in SEQ ID NO. 3 and 4.

On the other hand, protein samples of the four groups of HASMC are prepared by harvesting the four groups of HASMC in RIPA buffer (Invitrogen, CA, USA) firstly and centrifuged at 4° C. 1,2000 rpm to obtain supernatants as total cell lysate of the four groups of HASMC. In the present embodiment, the four groups of protein lysate are denatured in a mixture of 2% SDS, 10 mM dithiothreitol, 60 mM Tris-HCl (pH6.8) and 0.1% bromphenol blue, and then analyzed by polyacrylamide/SDS gel. Data obtained from the polyacrylamide/SDS gel analysis are further transferred to PVDF membrane for western blot assay. The PCDF membrane is sequentially blocked in 1×PBS buffer and 5% nonfat milk at room temperature for 1 hour, incubated in PBST buffer and anti-LOX-1 antibody (Sigma-Aldrich Inc, MO, USA) at 4° C. for overnight, incubated with a secondary antibody conjugated to horseradish peroxidase (Sigma-Aldrich Inc, MO, USA) at room temperature for 1 hour, and finally detected by Bio-Rad ChemiDoc XRS System.

In FIG. 2, both of the mRNA levels and protein levels of LOX-1 are enlarged by the increase of oxLDL, and therefore, it is suggested that oxLDL can induce the expression of LOX-1 in human aortic smooth muscle cell in a dose-dependent manner.

For further proving the relation between oxLDL, LOX-1, and the proliferation/migration of aortic smooth muscle cells, a LOX-1 inducer and a LOX-1 suppressor are prepared and used in the present invention for studying the connection of LOX-1 and the proliferation/migration of HASMC. In the present embodiment, a pEGFP-LOX-1 plasmid comprised full-length LOX-1 cDNA is used as the LOX-1 inducer. The pEGFP-LOX-1 is generated by PCR amplifying the full-length LOX-1 cDNA with a primer pair set forth in SEQ ID NO: 5 and 6, cloning the amplified full-length LOX-1 cDNA into pGEM-T Easy vector (Promega corporation, CA, USA) for sequence confirmation, and then further cloning into pEGFP-N3 vector (Promega corporation, CA, USA) without green fluorescent protein (GFP) fusion. Specifically, the PCR program of the present embodiment includes an initial step at 95° C. for 5 minutes; an extending step comprising 40 cycles of 94° C. for 1 minutes, 59° C. for 1 minutes and 72° C. for 1 minutes; and a final extension step at 72° C. for 10 mins. Moreover, the pEGFP-N3 vector is digested by BamHI/NotI before the cloning, in order to deleting GFP gene.

Figure 3:
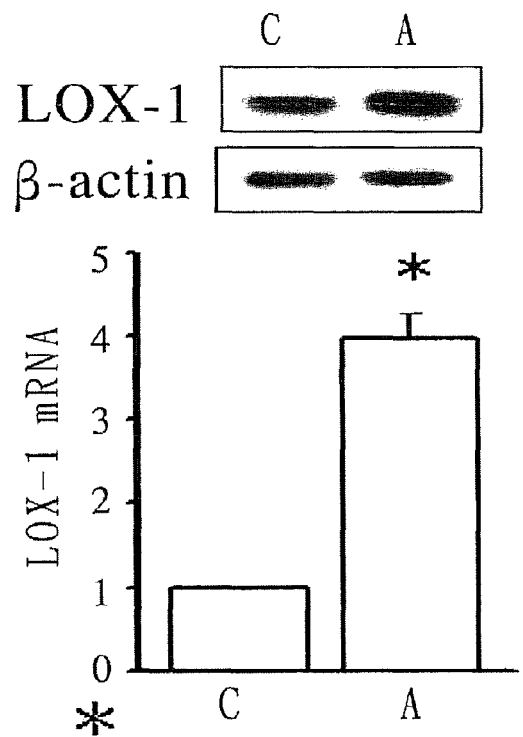
FIG. 3 is a bar chart and a western blot data illustrating the expression of LOX-1 in human aortic smooth muscle cells (HASMC)
Figure 4:
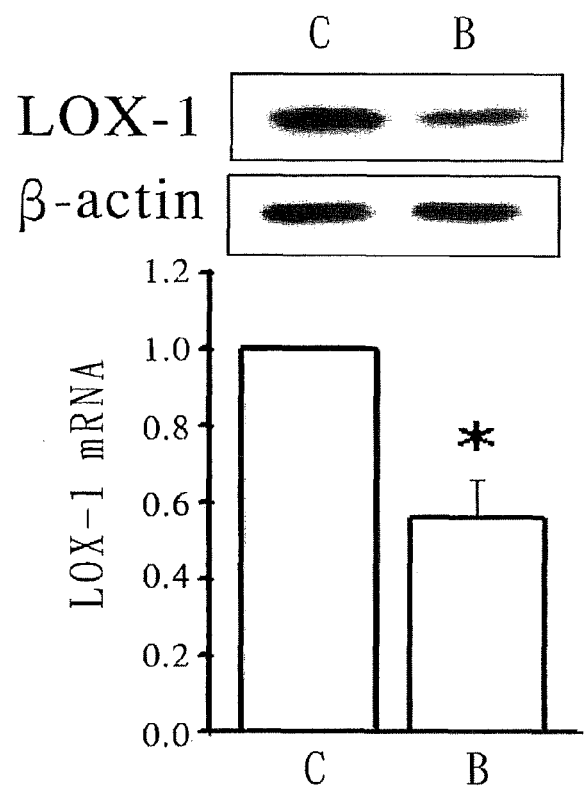
FIG. 4 is a bar chart and a western blot data illustrating the expression of LOX-1 in HASMC.

The LOX-1 suppressor of the present embodiment is a LOX-1 shRNA purchased from National RNAi Core Facility in Taiwan, R.O.C, and which is mainly designed according to the LOX-1 cDNA (NM_002543.3). With reference to FIGS. 3 and 4, the transfection of LOX-1 shRNA or the pEGFP-LOX-1 into the HASMC can shut down or over-express, respectively, the expression of LOX-1 in the HASMC.

As summarized in TABLE 1, six groups of the HASMC are prepared, including groups of (L1), being a control; (L2), treated with 404 ml oxLDL; (L3), treated with co-transfection of the pEGFP-LOX-1; (L4), treated with 40 μg/ml oxLDL and co-transfection of the pEGFP-LOX-1; (L5), treated with co-transfection with the LOX-1 shRNA; and (L6), treated with 40 μg/ml oxLDL and co-transfection of the LOX-1 shRNA, for over-expressing or knocking down LOX-1 of the HASMC. In the present embodiment, the degrees of cell proliferation in each group are measured by using WST-1 cell proliferation assay (Millipore, Mass., USA). Specifically, the six groups of HASMC are seeded in a 12-well plate till at a density of $10^5$ cells/well, and then proceeded to the following treatment of oxLDL and co-transfection with pEGFP-LOX-1 or LOX-1 shRNA. After 24 hours of transfection, the absorption of each group of HASMC is measured by a microplate reader under 440 nm and 650 nm.

TABLE 1

Assignment of Six Groups of HASMC

| Groups | Culture | Transfection |
|---|---|---|
| L1 | — | — |
| L2 | oxLDL | — |
| L3 | — | pEGFP-LOX-1 |
| L4 | oxLDL | pEGFP-LOX-1 |
| L5 | — | LOX-1 shRNA |
| L6 | oxLDL | LOX-1 shRNA |

Figure 5:
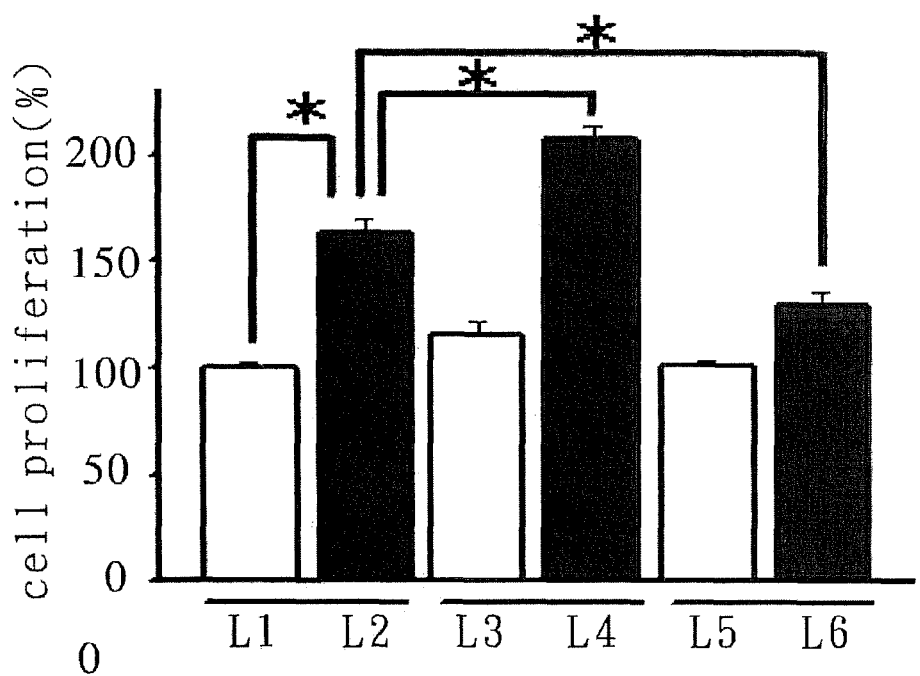
FIG. 5 is a bar chart illustrating the proliferation degree of HASMC in groups (L1) to (L6)
Figure 6:
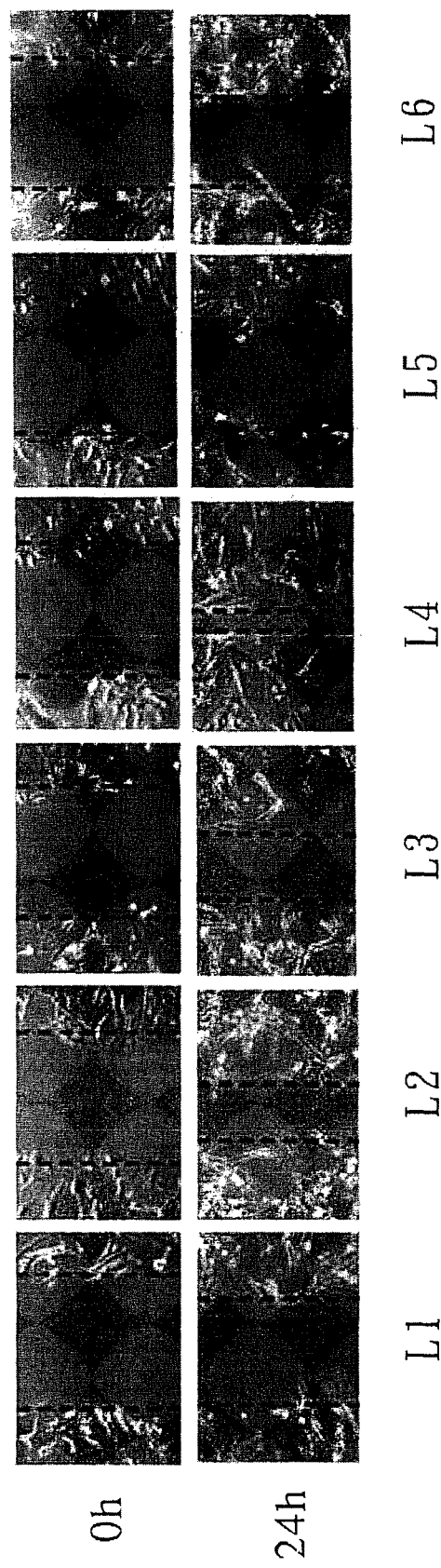
FIG. 6 is photo showing the proliferation and migration of HASMC in groups (L1) to (L6)

FIGS. 5 and 6 show the degree of cell proliferation of the six groups, wherein the transfection of the pEGFP-LOX-1 dramatically advance the oxLDL-mediated cell proliferation, with around two times of increase than that of the control (L1). Yet, knockdown of LOX-1 by the LOX-1 shRNA decrease the proliferation of the HASMC. It is believed that oxLDL not only induces the expression of LOX-1, also binds to LOX-1 and mediates the inflammatory response of aortic smooth muscle cells.

Figure 7:
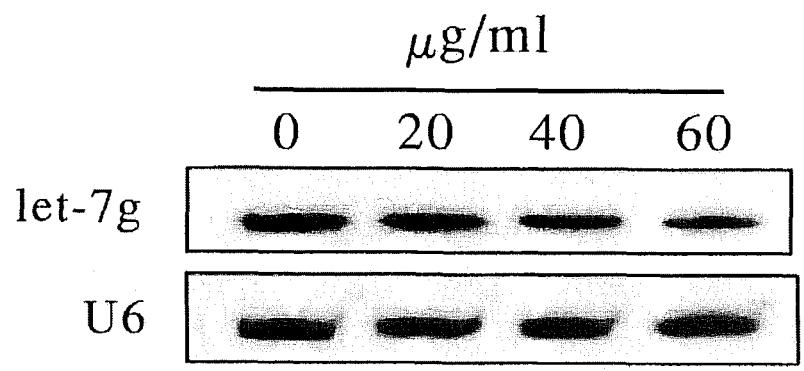
FIG. 7 is a northern blot data illustrating the expression of let-7g under various levels of oxLDL.
Figure 8:
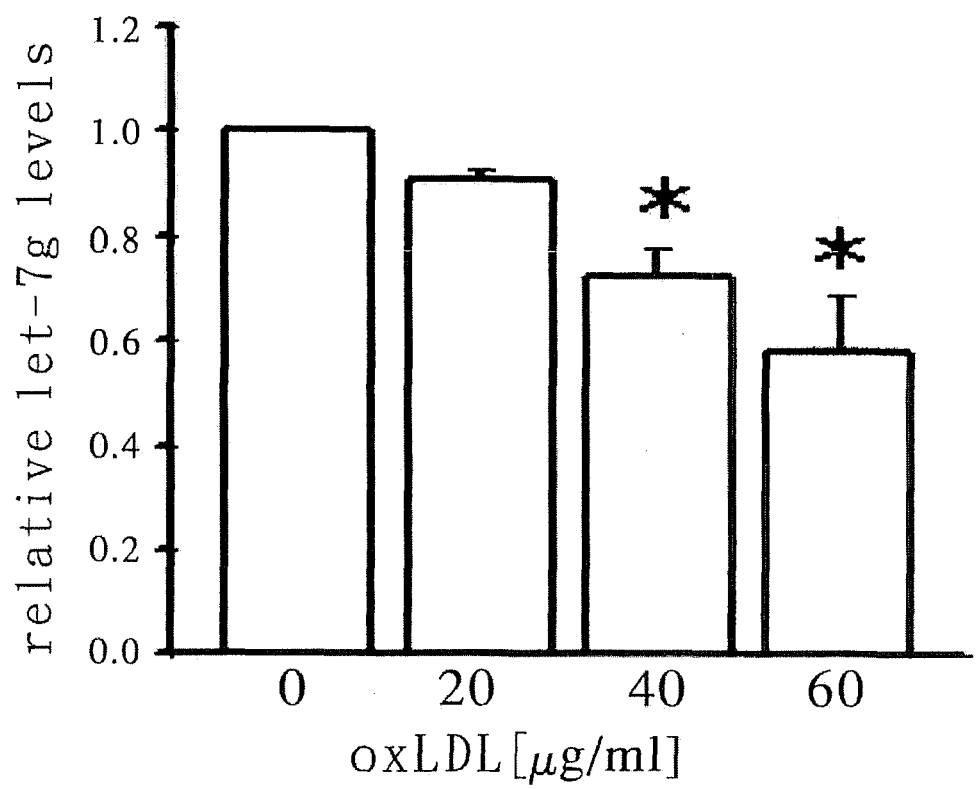
FIG. 8 is a bar chart illustrating relative let-7g levels under various levels of oxLDL.

In FIGS. 7 and 8, there is the relationship between oxLDL and let-7g in the HASMC. In the present embodiment, the HASMC are treated with various levels of oxLDL, for example 0, 20, 40 and 60 μg/ml, in order to monitor and to recorder the effect of oxLDL on let-7g. Similarly, the HASMC cell is grown in a 6-well plate till at a density of $2 \times 10^5$ cell/well, and then randomly assigned into plural groups with the treatment of 0, 20, 40 and 60 μg/ml oxLDL individually for 24 hours. Finally, total RNA samples of each group of HASMC are analyzed by northern blot and quantified real time PCR via above protocols. In the present embodiment, a primer pair of let-7g as set forth in SEQ ID NO: 7 and 8 is used in the teal time PCR analysis according to the same PCR program described above. Also, the northern blot of the present invention is determined by using a miRNA northern blot assay kit (Applied Biosystems, CA, USA). Precisely, the total RNA samples of each group is fractionated on 15% TBE urea-PAGE, blotted on membranes and hybridized with biotin labeled let-7g and U6 probe (Signosis Inc, CA, USA).

In FIGS. 7 and 8, the mRNAs of let-7g in HASMC decreases by increasing the dose of oxLDL. It is suggested that oxLDL can inhibit the expression of let-7g in arterial smooth muscle cells, particularly, in a dose dependent manner.

Figure 9:
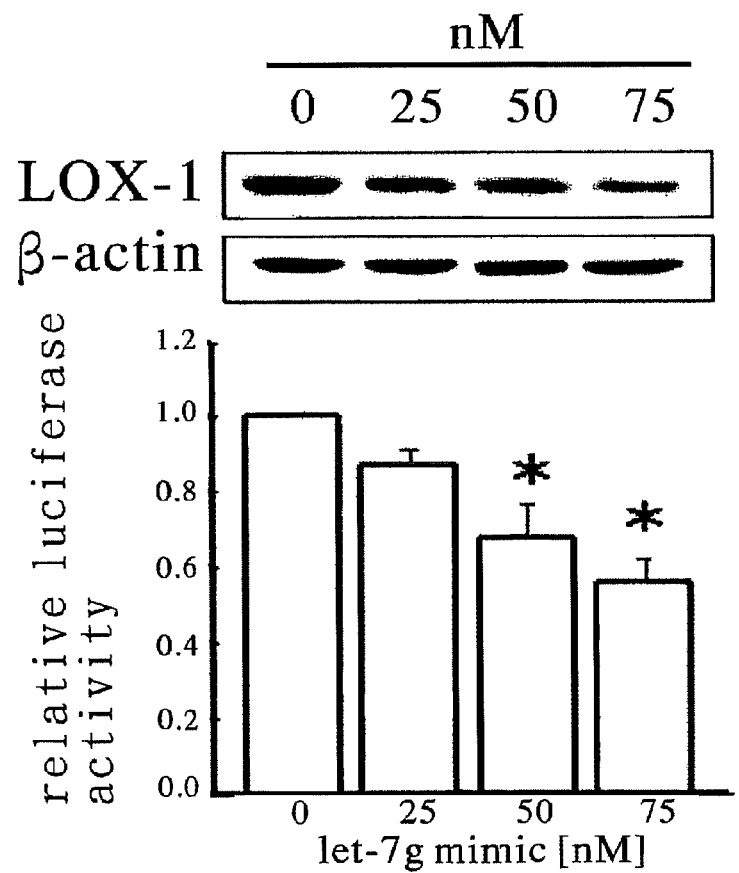
FIG. 9 is a bar chart and a western blot data illustrating the expression of LOX-1 under various levels of let-7g mimic.

In FIG. 9, the expression of LOX-1 in HASMC under various levels of let-7g is monitored and reordered. In the present invention, an analogue of let-7g, let-7g mimic (Applied Biosystems, CA, USA), is used to demonstrate the expression and function of let-7g in HASMC. Precisely, various levels of the let-7g mimic including 0, 25, 50 and 75 nM, are transiently transfected into the HASMC individually to analyze the expression of LOX-1 by real time PCR and western blot. The protein and the total RNA of the HASMC are prepared as the above protocol. Also, the primer pair of LOX-1 set forth in SEQ ID NO. 3 and 4 is used in the real time PCR of the present embodiment.

As it is shown in FIG. 9, both of the mRNAs levels and the protein levels of LOX-1 are decreased by the increased dose of the let-7g mimic. It is noted that transfection of the let-7g mimic to the HASMC significantly reduces the expression of LOX-1, particularly in a dose-dependent manner.

Figure 10:
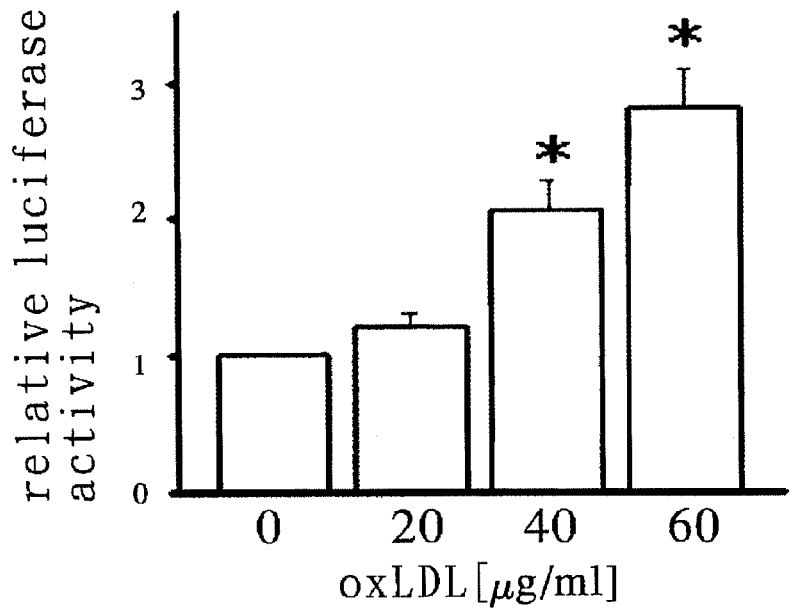
FIG. 10 is a bar chart illustrating the relationship between the 3'UTR region of LOX-1 and oxLDL.
Figure 11:
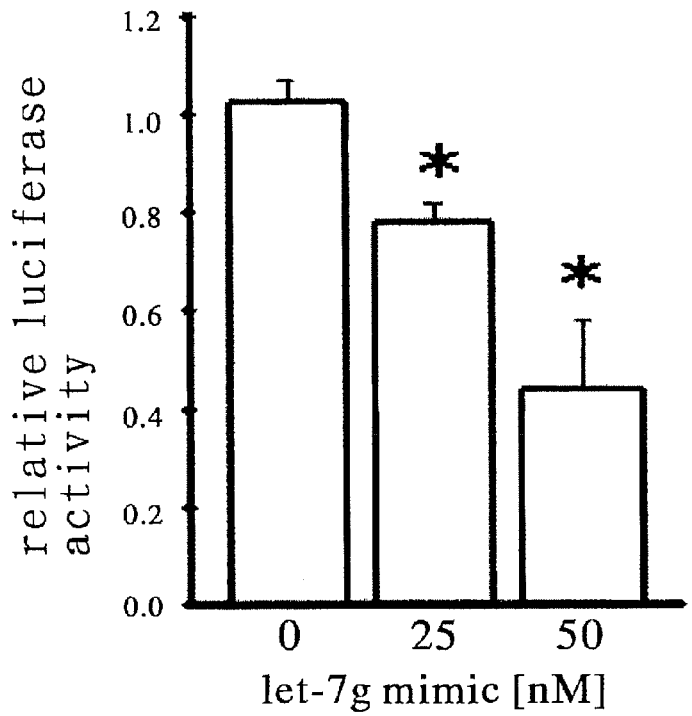
FIG. 11 is a bar chart illustrating the relationship between the 3'UTR region of LOX-1 and let-7g mimic.

Referring to FIGS. 10 and 11, the relationship between oxLDL, LOX-1 and let-7g is further identified. In the present invention, the 3'UTR region of LOX-1 is cloned into a commercial vector, preferably downstream of a reporter gene, such as a luciferase gene, for the sake of studying the effect of oxLDL and let-7g on LOX-1 by estimating the activity of the reporter gene. In the present embodiment, a pMIR-LOX-1-3UTR vector is obtained by PCR amplifying the 3'UTR region of LOX-1 in the chromosome DNA of HASMC with a primer pair set forth in SEQ ID NO. 9 and 10; and cloning the amplified 3'UTR region of LOX-1 into a pMIR-REpORT luciferase vector (Ambion Inc, TX, USA). Furthermore, the pMIR-LOX-1-3UTR vector of the present embodiment is transfected into a human smooth muscle cell line CRL-1999 purchased from ATCC (Manassas, Va., USA) by using lipofectamine 2000 (Invitrogen Inc, CA, USA). In the present embodiment, the CRL-1999 cell line of the present embodiment is incubated in F12K Kaighn's modification medium (GIBCO-BRL, MD, USA) with various levels of oxLDL and let-7g mimic, followed by analyzed the activity of luciferase by a Luciferase Assay System (Promega, WI, USA).

According to FIGS. 10 and 11, the activity of luciferase increases by the raise of oxLDL, but decrease by the raise of let-7g mimic. Therefore, it is believed that there is a feedback relationship between oxLDL, LOX-1 and let-7g, wherein the expression of LOX-1 is up-regulate by oxLDL, but is down-regulate by let-7g.

With reference to TABLE 2, the CRL-1999 cells are randomly assigned into seven groups including (U1) with co-transfection of the pMIR-LOX-1-3UTR only; (U2) with co-transfection of the pMIR-LOX-1-3UTR and treatment of oxLDL; (U3) with co-transfection of the pMIR-LOX-1-3UTR and the let-7g mimic; (U4) with co-transfection of the pMIR-LOX-1-3UTR and the let-7g mimic, and treatment of oxLDL; (U5) with co-transfection of the pMIR-LOX-1 mutant 3'UTR only; (U6) with co-transfection of the pMIR-LOX-1 mutant 3'UTR and treatment of oxLDL; (U7) with co-transfection of the pMIR-LOX-1 mutant 3'UTR and let-7 mimic for further validating the target of let-7g. In the present embodiment, the pMIR-LOX-1-3UTR and pMIR-LOX-1 mutant 3'UTR are transfected into CRL-1999 respectively by using the Lipofectamine 2000, wherein the pMIR-LOX-1 mutant 3'UTR comprises a mutant 3'UTR region of LOX-1. The pMIR-LOX-1 mutant 3'UTR of the present embodiment is obtained via site-directed mutagenesis carried out by using QuikChange® Site-Directed Mutagenesis Kit (Stratagene, Heidelberg, Germany). Specifically, a primer pair set forth in SEQ ID NO. 11 and 12 is used for PCR amplifying the mutant 3'UTR region of LOX-1. Finally, the luciferase activities of the seven groups of CRL-1999 are analyzed by using the Luciferase Assay System.

TABLE 2

Assignment of Seven Groups of CRL-1999 cells

| | Culture and Transfection | | |
|---|---|---|---|
| Groups | Constructs | oxLDL | let-7g mimic |
| U1 | pMIR-LOX-1-3UTR | − | − |
| U2 | pMIR-LOX-1-3UTR | + | − |
| U3 | pMIR-LOX-1-3UTR | − | + |
| U4 | pMIR-LOX-1-3UTR | + | + |
| U5 | pMIR-LOX-1 mutant 3'UTR | − | − |
| U6 | pMIR-LOX-1 mutant 3'UTR | + | − |
| U7 | pMIR-LOX-1 mutant 3'UTR | − | + |

Figure 12:
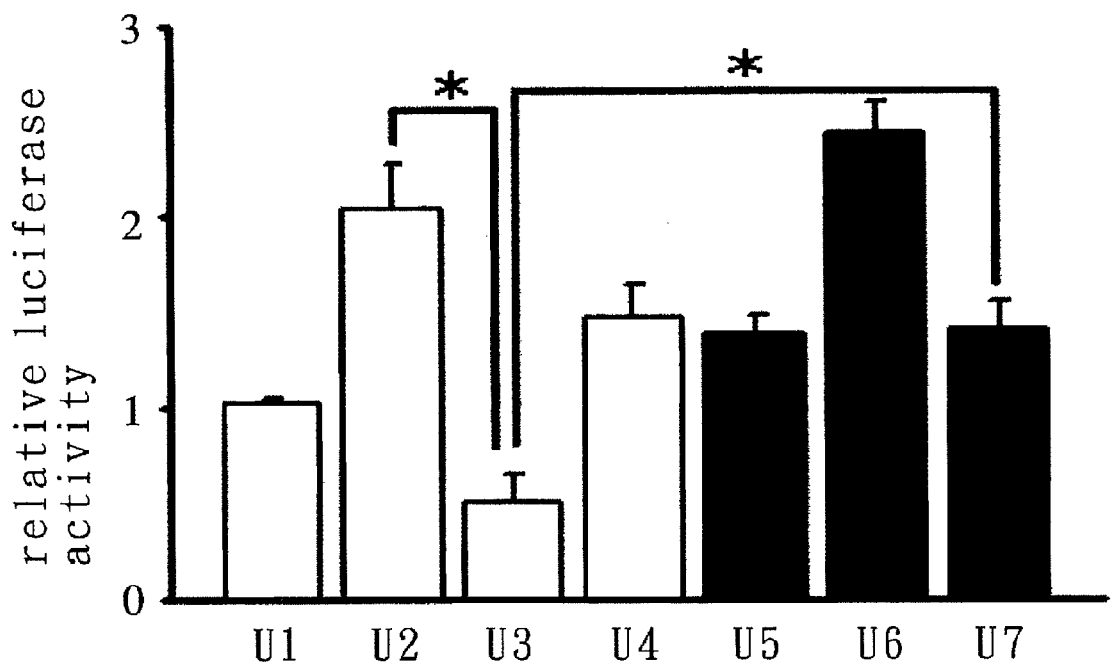
FIG. 12 is a bar chart illustrating the relationship between LOX-1, let-7g mimic and oxLDL.

FIG. 12 indicates that let-7g targets to the 3'UTR region of LOX-1 to suppress the expression of LOX-1, and therefore, the mutant 3'UTR region of LOX-1 will interfere with the effect on let-7g on LOX-1.

Next, for further proving the detailed mechanism of the feedback relationship between oxLDL, let-7g, and LOX-1, 1.5k bp upstream region of let-7g promoter is cloned into a reporter vector, preferably upstream of a reporter gene (for example luciferase). With such arrangement, the effect of oxLDL on let-7g promoter can be examined by estimating the activity of the reporter gene.

Figure 13:
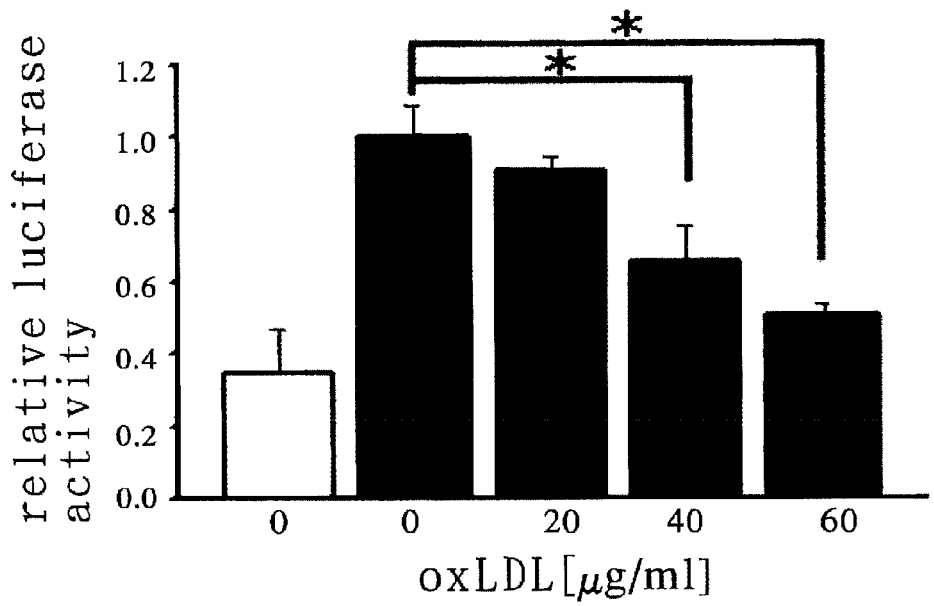
FIG. 13 is a bar chart illustrating the relationship between let-7g promoter and oxLDL.

In FIG. 13, the effects of oxLDL on let-7g promoter are summarized. In the present embodiment, a pGL3-let-7g-1.5g vector, comprising the 1.5k bp upstream region of let-7g promoter, is constructed by PCR-amplifying the fragment of let-7g promoter with a primer pair set forth in SEQ ID NO. 13 and 14; and cloning the amplified fragment of let-7g promoter into a pGL3 vector (Promega, WI, USA). Moreover, the pGL3-let-7g-1.5 g vector of the present embodiment is further transfected into the CRL-1999 cell line, in order to monitor and record the effect of 0, 20, 40 and 60 g/ml oxLDL on let-7g promoter based on the luciferase activity of transfected CRL-1999.

According to FIG. 13, the activity of let-7g promoter decrease by the raise of oxLDL levels. As a result, oxLDL inhibits the activity of let-7g promoter, and down-regulates the expression of let-7g in aortic smooth muscle cells, particularly in a dose-dependent manner.

To refer to TABLE 3, several reporter constructs of let-7g promoter, including pGL3-let-7g-1.0k and pGL3-let-7g-0.5k are designed and tested in the present invention, for further identifying the core region of let-7g promoter. In the present embodiment, the pGL3-let-7g-1.0k and pGL3-let-7g-0.5k are prepared by using the pGL3-let-7g-1.5k as a temple to isolate 1.0k bp and 0.5k bp upstream region of let-7g promoter with primers set forth in SEQ ID NO. 13, 15 and 16; and cloning the isolated 1.0k bp and 0.5k bp upstream region of let-7g promoter into the pGL3 vector respectively. The pGL3-let-7g-1.0k and pGL3-let-7g-0.5k, comprising 1.0k bp or 0.5k bp upstream region of let-7g promoter individually. In the present embodiment, the CRL-1999 cells are prepared and randomly divided into five groups including (D1), with co-transfection of pGL3-let-7g-1.5k and treatment of 40 µg/ml oxLDL; (D2), with co-transfection of pGL3-let-7g-1.0k and treatment of 40 µg/ml oxLDL; (D3), with co-transfection of pGL3-let-7g-0.5k and treatment of 40 µg/ml oxLDL; (D4), with co-transfection of pGL3-let-7g-1.5k; and (C) as a control, for identified the effect of the let-7g promoter deletion on the relationship between oxLDL and let-7g.

TABLE 3

Reporter Constructs of Let-7g Promoter

| Groups | Reporter Constructs | Culture (oxLDL) |
|---|---|---|
| D1 | pGL3-let-7g-1.5k | + |
| D2 | pGL3-let-7g-1.0k | + |
| D3 | pGL3-let-7g-0.5k | + |
| D4 | pGL3-let-7g-1.5k | − |
| C | pGL3 | |

Figure 14:
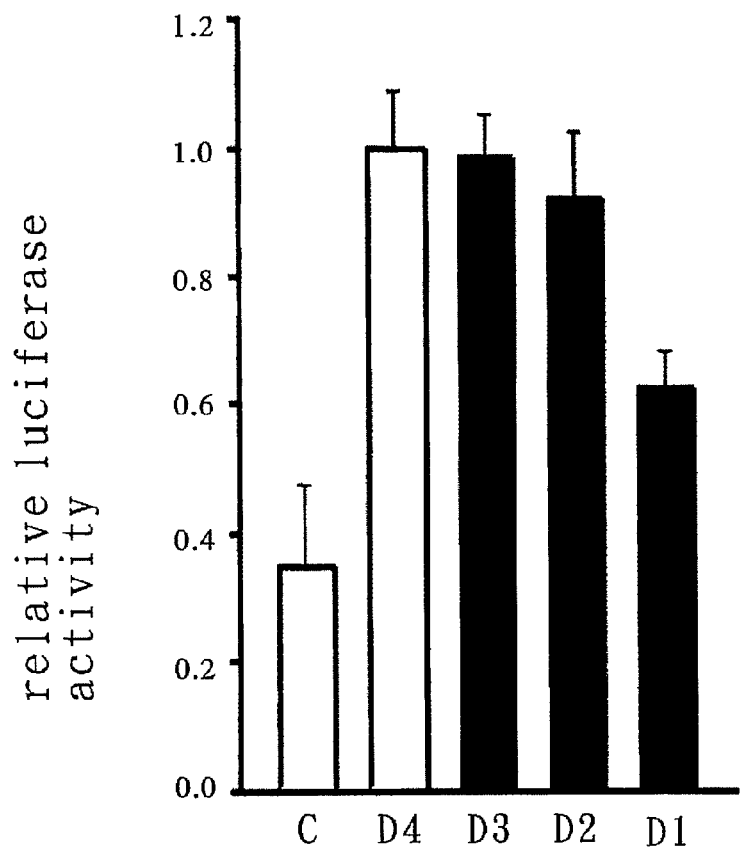
FIG. 14 is a bar chart illustrating the luciferase activity of groups (P1) to (P4)

Data in FIG. 14 shows that the core region of let-7g is at 1k to 1.5k bp upstream region of let-7g promoter.

Additionally, in accordance with FIG. 15, three putative transcription factor binging site, including OCT-1 hinging site, GATA-1 binding site and C/EBPb binding site, are predicted via TFSEARCH software (ver 1.3), wherein OCT-1, GATA-1 and C/EBPb bind to $1427^{th}$ to $1400^{th}$, $1177^{th}$ to $1186^{th}$, and $1062^{th}$ to $1075^{th}$ upstream region of let-7g promoter respectively.

In TABLE 4, the CRL-1999 cells are randomly assigned into four groups, having (P1), with co-transfection of the pGL3-let-7g-1.5k only; (P2), with co-transfection of the pGL3-let-7g-1.5k and treatment of oxLDL; (P3), with co-transfection of pGL3-let-7g mutant only; and (P4), with co-transfection of the pGL3-let-7g mutant and treatment of oxLDL, for verifying the binding of transcription factor OCT-1 and let-7g, as well as the effect of oxLDL on the binding of OCT-1 and let-7g. In the present embodiment, the pGL3-let-7g-1.5k and pGL3-let-7g mutant are transfected into CRL-1999 respectively by using the Lipofectamine 2000, wherein the pGL3-let-7g mutant has five nucleotides mutant on the OCT-1 binding site of let-7g promoter. The pGL3-let-7g mutant of the present invention is generated via site-directed mutagenesis carried out by using the QuikChange® Site-Directed Mutagenesis Kit, and in which the mutant region on OCT-1 binding site of let-7g promoter is amplified by a primer pair set forth in SEQ ID NO. 17 and 18. Finally, the luciferase activities of the four groups of CRL-1999 are analyzed by using the Luciferase Assay System.

TABLE 4

Assignment of Four Groups of CRL-1999 cells

| Groups | Constructs | oxLDL |
| --- | --- | --- |
| P1 | pGL3-let-7g-1.5k | − |
| P2 | pGL3-let-7g-1.5k | + |
| P3 | pGL3-let-7g mutant | − |
| P4 | pGL3-let-7g mutant | + |

FIG. 16 points out that oxLDL suppress the expression of let-7g in aortic smooth muscle cells due to the binding of OCT-1 on the upstream region of let-7g promoter. Yet, a mutant on the OCT-1 binding site of let-7g promoter will interfere with the inhibition of oxLDL on let-7g.

Figure 17:
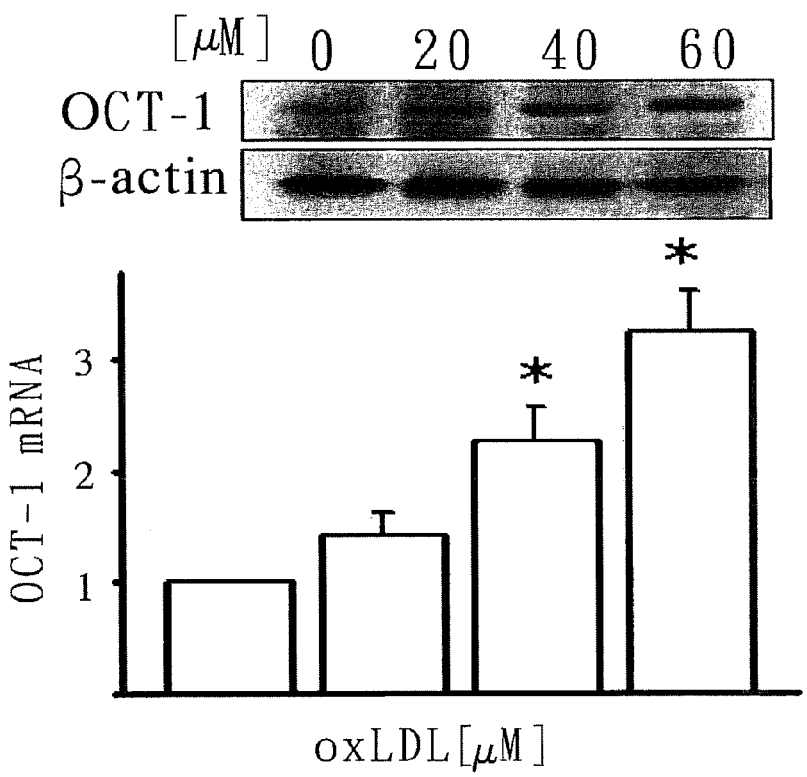
FIG. 17 is a bar chart and a western blot data illustrating the expression of OCT-1 under various levels of oxLDL.

The following trials stress on the mechanism between let-7g, LOX-1, oxLDL and OCT-1. In FIG. 17, the expression of OCT-1 under various levels of oxLDL is shown. In the present embodiment, the HASMC cell is treated with 0, 20, 40, and 60 μg/ml of oxLDL individually for 24 hours, and then total RNA samples and protein samples of the HASMC are prepared and analyzed by the real time PCR and western blot assay of the present invention. Precisely, the preparation of the total RNA samples and the protein samples of the HASMC, also the PCR program and western blot assay are performed according to the above protocols. Moreover, a primer pair of OCT-1 set forth in SEQ ID NO. 19 and 20 is designed and used in real time PCR analysis, and a commercial OCT-1 antibody (Sigma-Aldrich Inc, MO, USA) is used in western blot assay.

To refer to FIG. 17, the expression of OCT-1 in the HASMC increases by the raise of oxLDL levels, particularly in a dose-dependent manner.

According to TABLE 5, an OCT-1 suppressor is prepared and used in the present invention for studying the mechanism of OCT-1 in oxLDL-mediated signal transduction pathway of the HASMC. In the present embodiment, the OCT-1 suppressor is an OCT-1 shRNA obtained from National RNAi Core Facility in Taiwan, R.O.C, for the sake of turning down the expression of OCT-1 in aortic smooth muscle cells.

TABLE 5

Groups Assignment of HASMC

| Groups | Transfection and Culture | |
| --- | --- | --- |
| O1 | — | — |
| O2 | — | oxLDL |

TABLE 5-continued

Groups Assignment of HASMC

| Groups | Transfection and Culture | |
| --- | --- | --- |
| O3 | OCT-1 shRNA | — |
| O4 | OCT-1 shRNA | oxLDL |

In the present embodiment, the HASMCs are randomly assigned into four groups, including groups (O1), as a control; (O2), with treatment of oxLDL; (O3), with co-transfection of the OCT-1 shRNA; and (O4), with co-transfection of the OCT-1 shRNA and treatment of oxLDL, wherein total RNA samples and protein sample of those groups are extracted and analyzed by the real time PCR and the western blot of the present invention. Precisely, the preparation of the total RNA samples and the protein samples of the four groups of HASMC, also the PCR program and western blot assay are performed according to the above protocols. Moreover, primer pairs set forth in SEQ ID NO. 3, 4, 7, and 8, and the OCT-1 antibody and LOX-1 antibody are used respectively in real time PCR or western blot assay.

Figure 18:
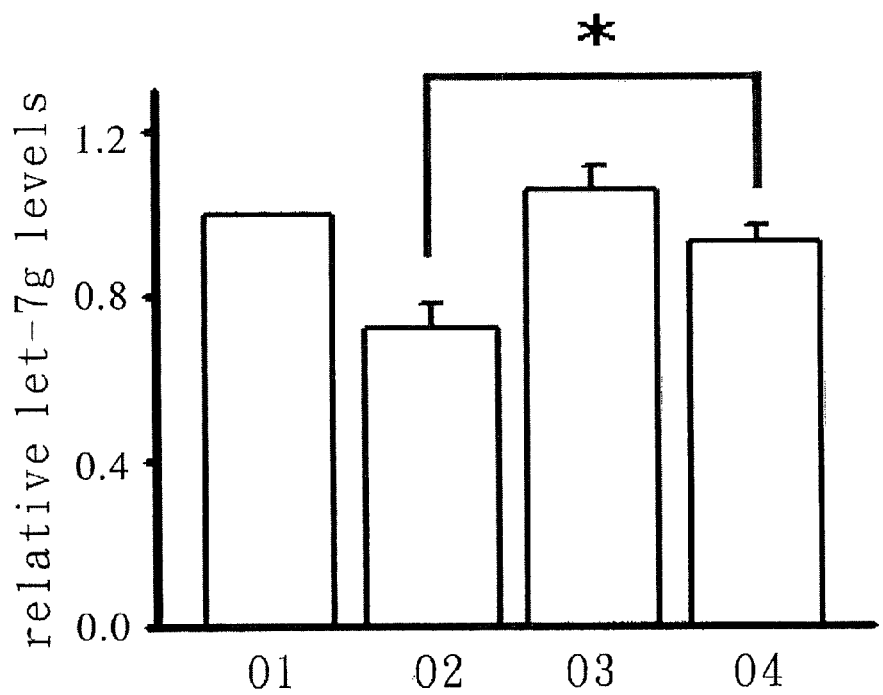
FIG. 18 is a bar chart illustrating relative let-7g levels in groups (O1) to (O4)
Figure 19:
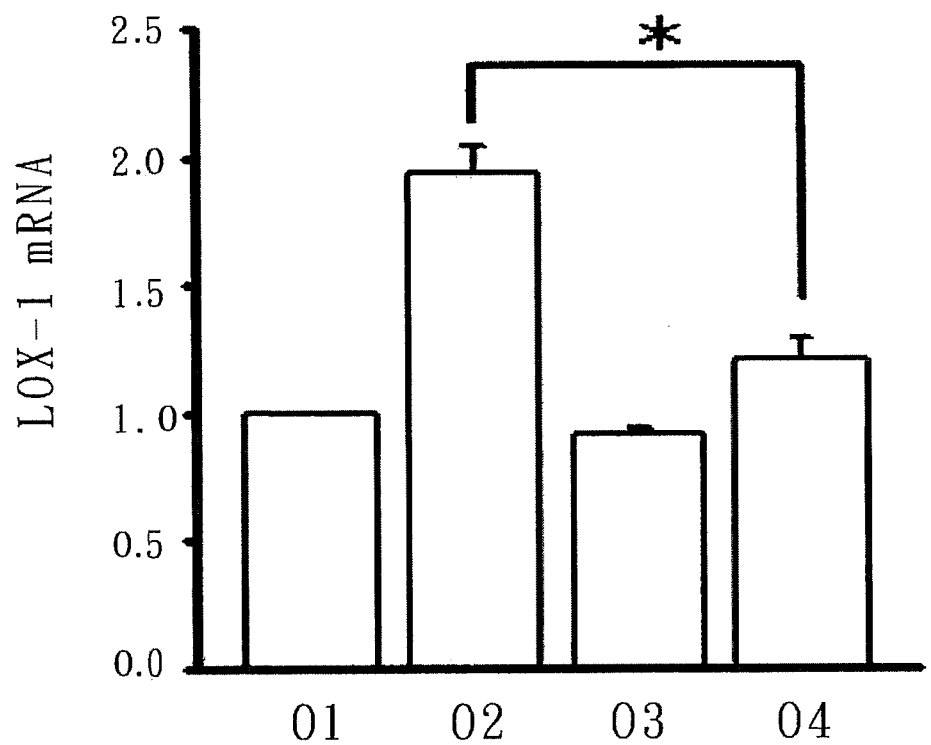
FIG. 19 is a bar chart illustrating the expression of LOX-1 in groups (O1) to (O4)
Figure 20:
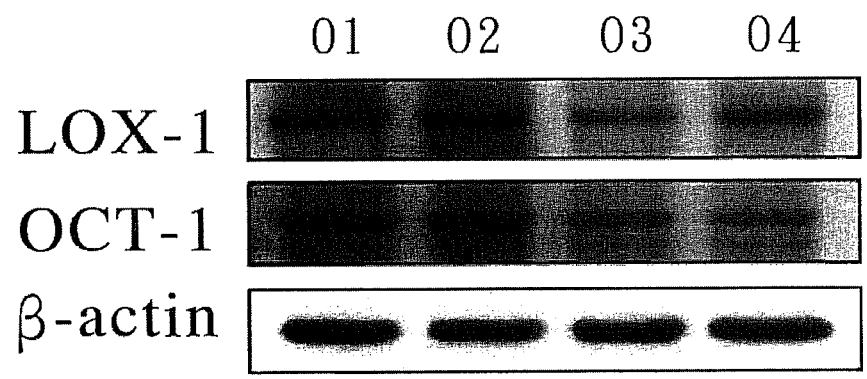
FIG. 20 is a western blot data illustrating the expression of LOX-1 and OCT-1 in groups (O1) to (O4)

As shown in FIGS. 18 and 19, both of the oxLDL-mediated inhibition on let-7g, and the oxLDL induced LOX-1 expression are knocked down due to the block of OCT-1. Furthermore, according to FIG. 20, the expression of LOX-1 is decreased by the knockdown of OCT-1. It is noticeable that oxLDL upregulate the expression of LOX-1 and OCT-1, but down-regulates the expression of let-7g in aortic smooth muscle cells.

Next, the present invention proves that protein kinase C (PKC) and intracellular $[Ca^{2+}]_i$ are involved in oxLDL-mediated let-7g down-regulation and oxLDL/LOX-1/OCT-1 pathway. In the present embodiment, chelerythrine (Merck, German) and MAPTAM (Invitrogen, CA, USA) are used as a suppressor of PKC or intracellular $[Ca^{2+}]_i$ to abolish the expression of PKC and intracellular $[Ca^{2+}]_i$ in aortic smooth muscle cells, in order to study the effect of PKC and intracellular $[Ca^{2+}]_i$ on LOX-1 and OCT-1 in aortic smooth muscle cells.

In TABLE 6, the HASMCs are randomly allocated to eight groups in the present embodiment, comprising groups of (I), being a control; (II), being treated with oxLDL; (III), being treated with of chelerythring; (IV), being treated with both of oxLDL and chelerythring; (V), being another control; (VI), being treated with oxLDL; (VII), being treated with MAPTAM; and (VIII) being treated with both of oxLDL and MAPTAM, and likewise, total RNA samples and protein samples of the eight groups of HASMCs are extracted and analyzed by real time PCR and western blot according to the protocol revealed above. In the present embodiment, primer pairs set forth in SEQ ID NO. 3, 4, 7, 8, 19, 20, the LOX-1 antibody, and the OCT-1 antibody are used respectively in PCR or western blot assay.

TABLE 8

Groups Assignment of HASMC

| Groups | Treatments | |
| --- | --- | --- |
| I | — | — |
| II | — | oxLDL |
| III | chelerythrine | — |
| IV | chelerythrine | oxLDL |
| V | — | — |

TABLE 8-continued

Groups Assignment of HASMC

| Groups | Treatments | |
|---|---|---|
| VI | — | oxLDL |
| VII | MAPTAM | — |
| VIII | MAPTAM | oxLDL |

Figure 21:
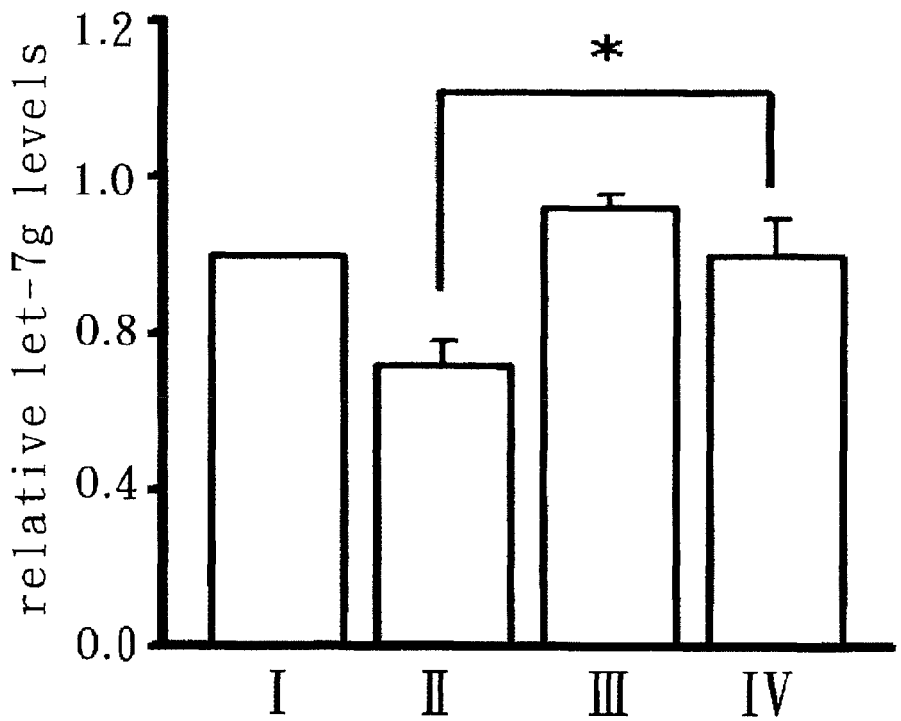
FIG. 21 is a bar chart illustrating relative let-7g levels in groups (I) to (IV)
Figure 22:
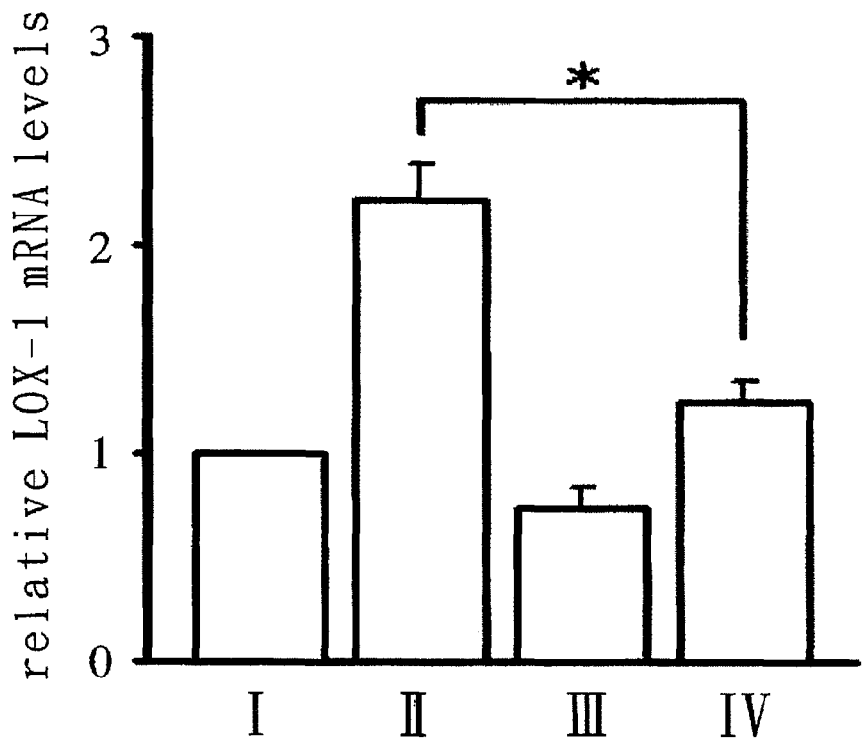
FIG. 22 is a bar chart illustrating relative LOX-1 levels in groups (I) to (IV)
Figure 23:
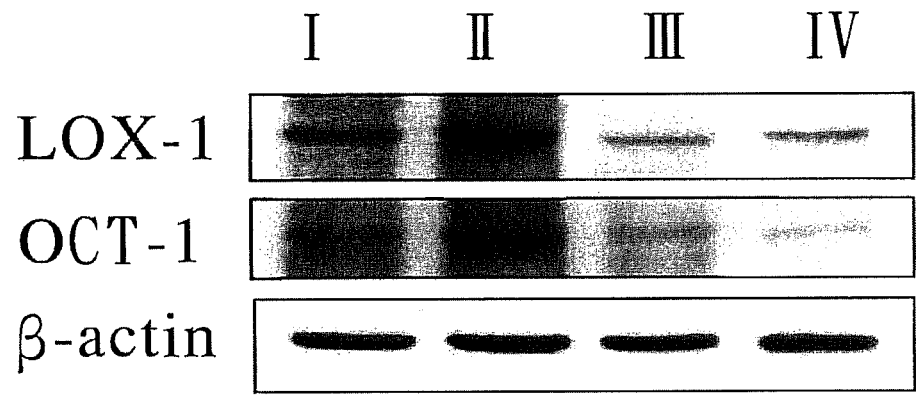
FIG. 23 is a western blot data illustrating the expression LOX-1 and OCT-1 in groups (I) to (IV)

FIGS. 21 and 22 demonstrate that the oxLDL-mediated inhibition on let-7g, and the oxLDL-induced LOX-1 expression are inhibited due to the suppression of PKC by chelerythrine. Additionally, FIG. 23 shows a significant decrease in the protein levels of OCT-1 and LOX-1 mediated by inhibiting PKC.

Figure 24:
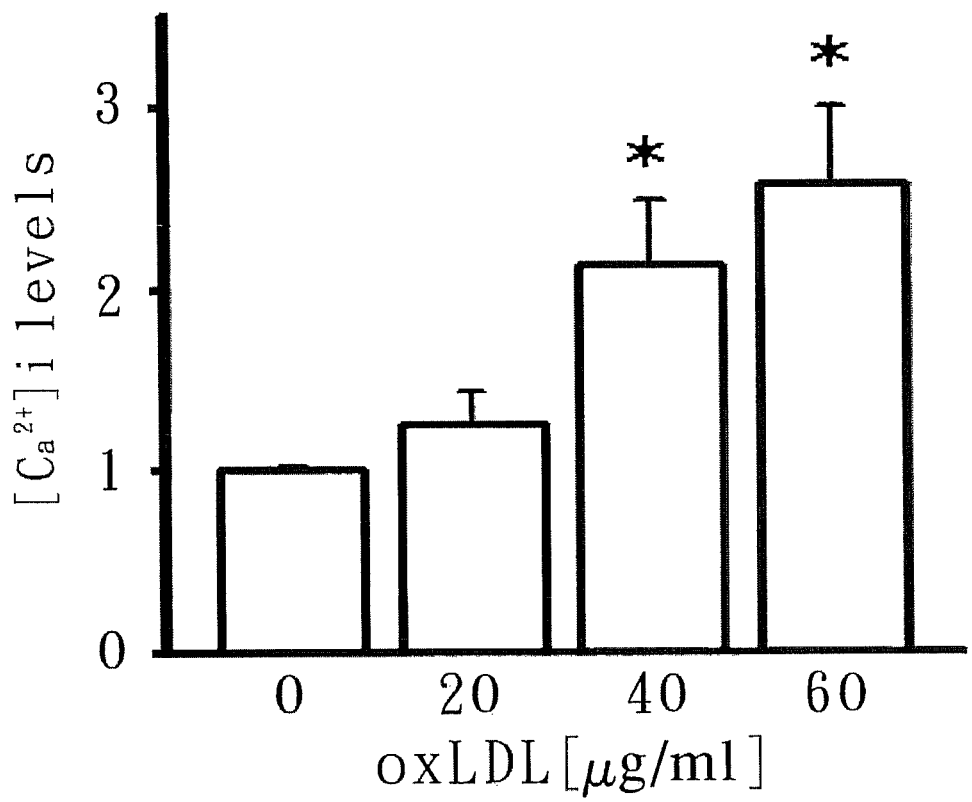
FIG. 24 is a bar chart illustrating the levels of intracellular $[Ca^{2+}]_i$ under various levels of oxLDL.

FIG. 24 points out the relationship between oxLDL and intracellular $[Ca^{2+}]_i$ in arterial smooth muscle cells. In the present embodiment, the HASMCs are assigned in to plural groups and treated with various levels, such as 0, 20, 40, and 60 μg/ml, of oxLDL individually for 15 minutes, followed by washed the plural groups of HASMC with a phosphate buffer and co-incubated with Fluo-4 AM (Invitrogen Inc, CA, USA) for 1 hour for fluor-developing. Finally, fluorescent intensities of in the plural groups of HASMC are measured by a fluorescence reader under 485 nm and 530 nm.

As it is shown in FIG. 24, intracellular $[Ca^{2+}]_i$ in HASMC raise according to the increase of oxLDL in a dose-dependent manner. It is supposed that oxLDL can induce the cell-permeability of calcium so as to advance the intracellular $[Ca^{2+}]_i$ in cells.

Figure 25:
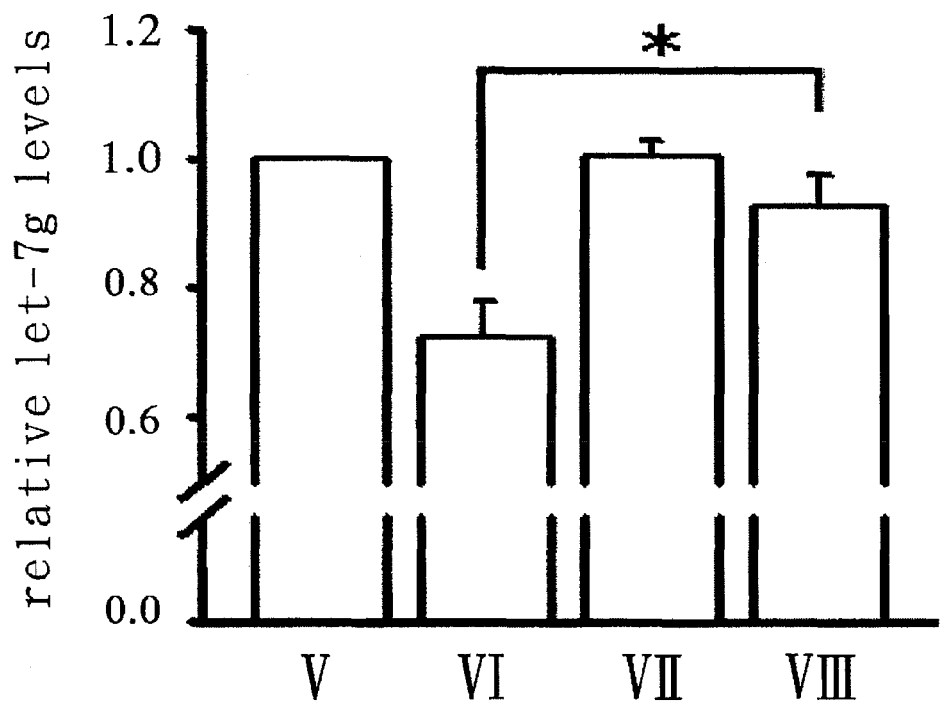
FIG. 25 is a bar chart illustrating relative let-7g levels in groups (V) to (VIII)
Figure 26:
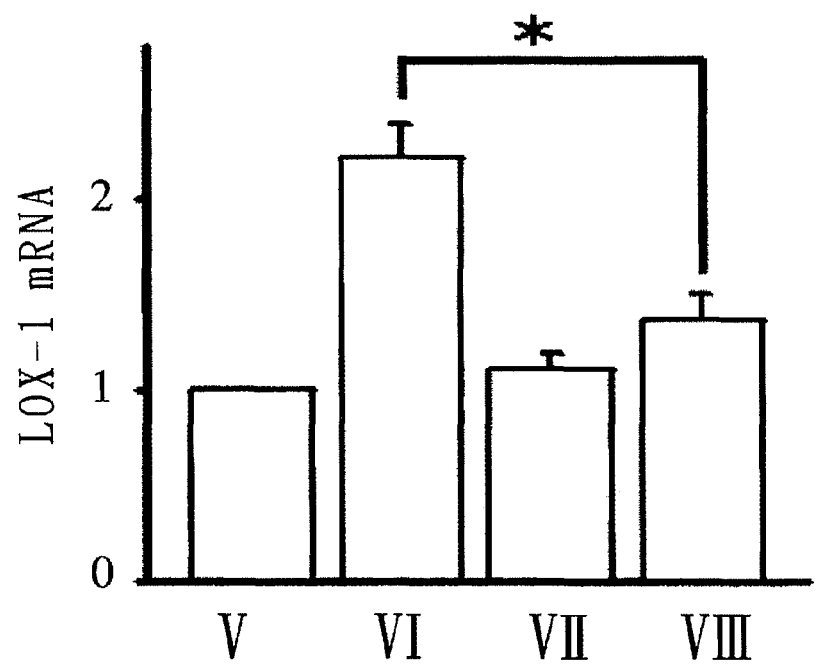
FIG. 26 is a bar chart illustrating LOX-1 mRNA levels in groups (V) to (VIII)
Figure 27:
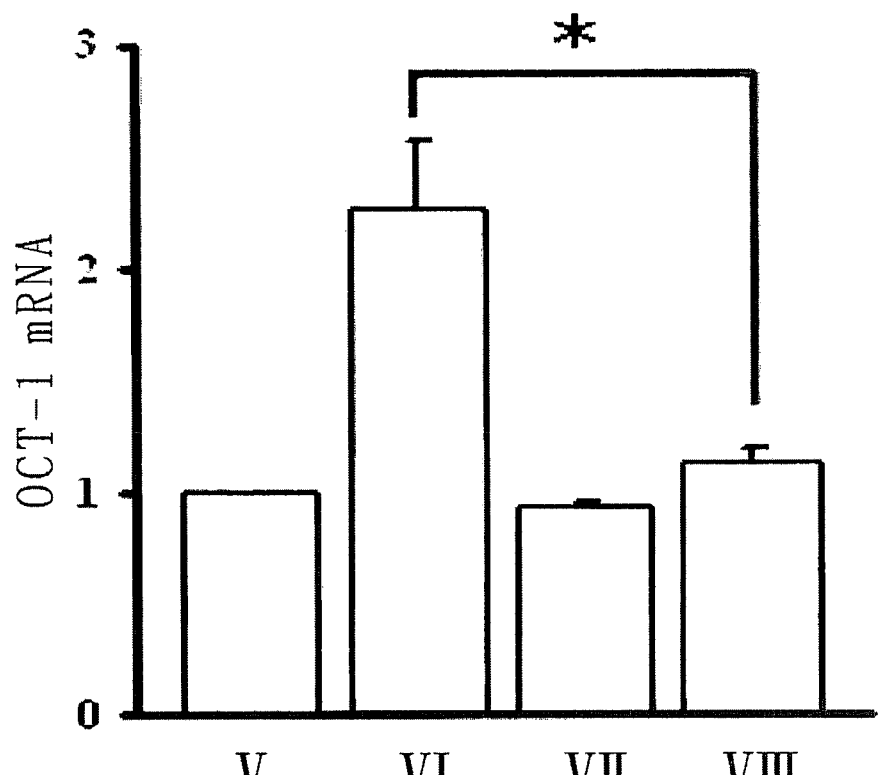
FIG. 27 is a bar chart illustrating OCT-1 mRNA levels in groups (V) to (VIII)
Figure 28:
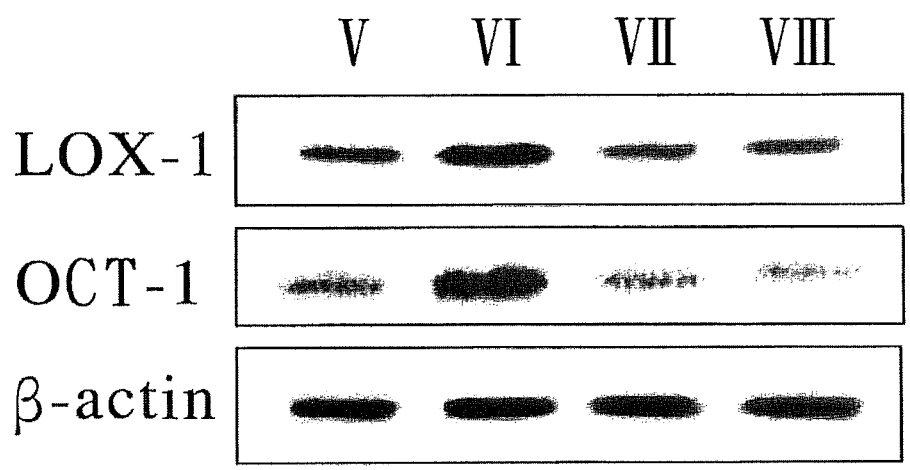
FIG. 28 is a western blot data illustrating LOX-1 and OCT-1 levels in groups (V) to (VIII)

FIGS. 25, 26 and 27 reveal that the oxLDL-mediated inhibition on let-7g, and the oxLDL-induced LOX-1 and OCT-1 expression are decreased due to the reduce of intracellular $[Ca^{2+}]_i$ by MAPTAM. Likewise, protein levels of OCT-1 and LOX-1 also have significant decrease because of the reduce of intracellular $[Ca^{2+}]_i$, as it is shown in FIG. 28.

In summary, there is a feedback regulation system between microRNA let-7g, transcription factor OCT-1, oxLDL and receptor LOX-1, wherein oxLDL decreases the expression of let-7g via a LOX-1/$[Ca^{2+}]_i$/PKC/OCT-1 pathway, and let-7g decreases the expression of LOX-1. Accordingly, the present invention provides a method of therapy of atherosclerosis, by providing microRNA let-7g, an analogue thereof or modified let-7g to inhibit the expression of LOX-1, as well as the binding of LOX-1 and oxLDL in arterial smooth muscle cells, so that the cell proliferation and migration caused by atherosclerosis can be improved.

Figure 29:
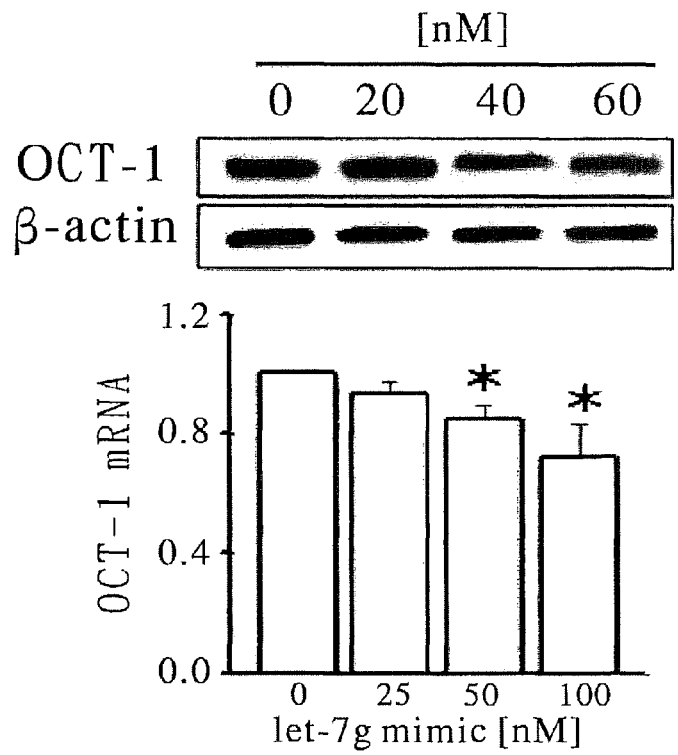
FIG. 29 is a bar chart and a western blot data illustrating the expression of OCT-1 under various levels of let-7g mimic.

With reference to FIG. 29, the let-7g mimic, being a suppressor of LOX-1, is transfected into the HASMCs of the present invention, and the expression of OCT-1 in the transfected HASMC is monitored and recorded. More specifically, various levels of let-7g mimic, such as 0, 25, 50, and 75 μg/ml, are respectively transfected into the HASMCs by the Lipofectamine 2000, and then total RNA samples and protein samples of the transfected HASMC are prepared and analyzed by real time PCR and western blot according to the protocols described above. Moreover, primer pairs set forth in SEQ ID NO. 19 and 20, and the OCT-1 antibody are used respectively in PCR or western blot analysis.

In FIG. 29, the expression of OCT-1 both in protein levels and mRNA levels decrease by the transfection of let-7g mimic, particular in a dose-dependent manner. It is validated that let-7g and the analogue thereof of the present invention can dramatically inhibit the expression of OCT-1 in arterial smooth muscle cells.

In TABLE 7, the HASMCs are randomly assigned into four groups including groups (a), being a control; (b), with treatment of oxLDL; (c), with co-transfection of let-7g mimic; and (d), with treatment of oxLDL and co-transfection of let-7g mimic, and then total RNA samples and protein samples of the four groups are collected and analyzed according to the protocols summarized above, in order to identify the effect of let-7g on the expression of LOX-1, OCT-1, and intraocular $[Ca^{2+}]_i$, and also the degree of HASMC proliferation.

TABLE 7

Groups Assignment of HASMC

| Groups | Treatments | |
|---|---|---|
| a | — | — |
| b | — | oxLDL |
| c | let-7gmimic | — |
| d | let-7gmimic | oxLDL |

Figure 30:
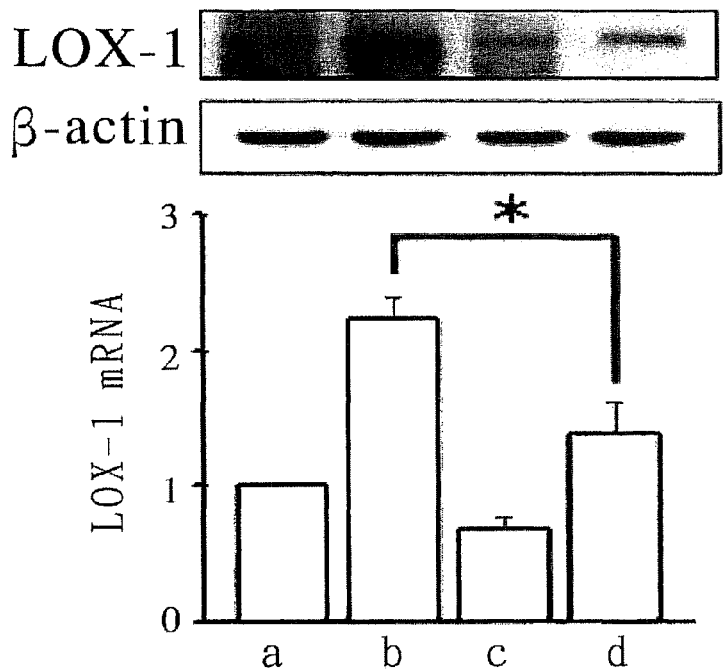
FIG. 30 is a bar chart and a western blot data illustrating the expression of LOX-1 in groups (a) to (d)
Figure 31:
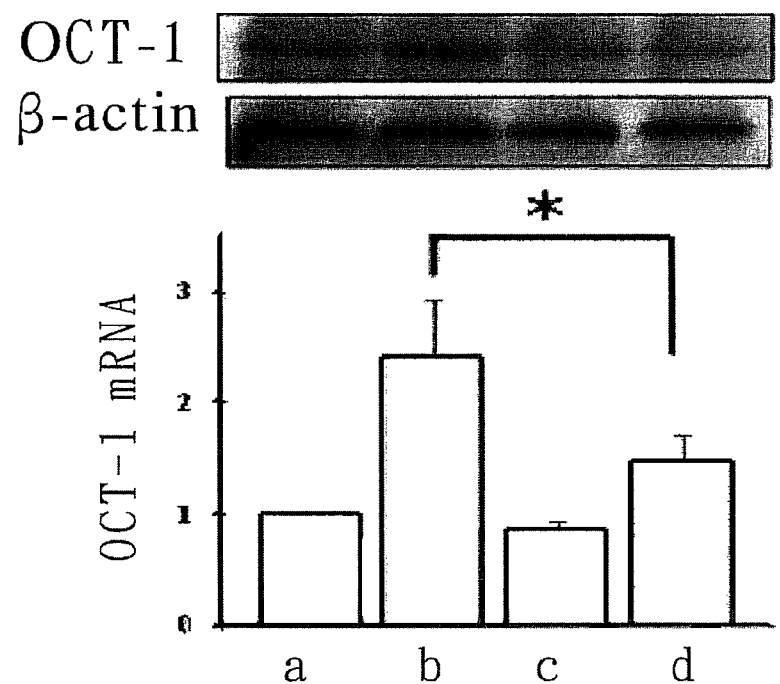
FIG. 31 is a bar chart and a western blot data illustrating the expression of OCT-1 in groups (a) to (d)
Figure 32:
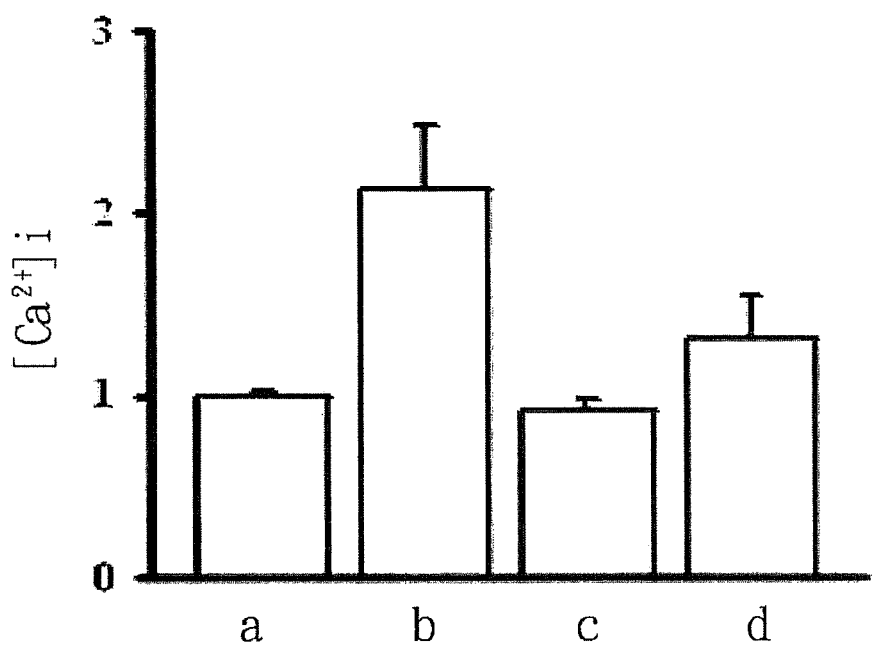
FIG. 32 is a bar chart illustrating the levels of intracellular $[Ca^{2+}]_i$ in groups (a) to (d)
Figure 33:
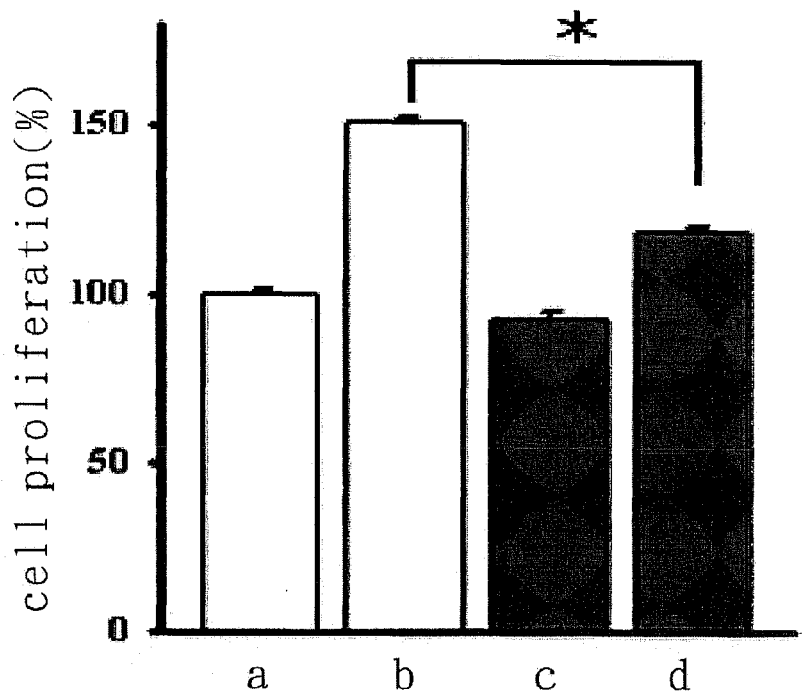
FIG. 33 is a bar chart illustrating the proliferation degree of HASMC in groups (a) to (d)
Figure 34:
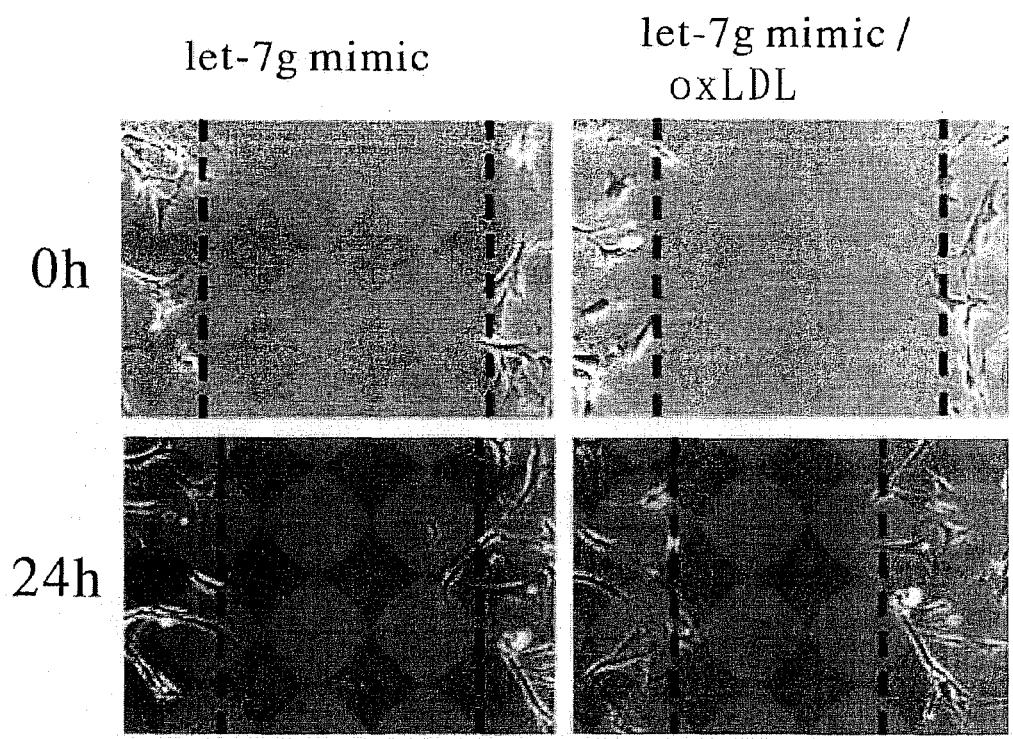
FIG. 34 is photo showing the proliferation and migration of HASMC.

FIGS. 30, 31 and 32 show that let-7g mimic significantly suppresses the oxLDL-induced OCT-1 expression, LOX-1 expression and intracellular $[Ca^{2+}]_i$ in HASMCs. Furthermore, in FIGS. 33 and 34, let-7g mimic clearly reduce oxLDL-induced HASMC proliferation and migration. Therefore, it is believed that let-7g and the analogue thereof of the present invention are sufficient to reduce the expression of LOX-1 and the downstream LOX-1/$[Ca^{2+}]_i$/PKC/OCT-1 signal pathway, and also to modulate the oxLDL-mediated cell proliferation and migration.

Through the present invention, the feedback relationship between oxLDL, LOX-1 and microRNA let-7g, and the detailed mechanism thereof is proved. Furthermore, it is demonstrated that microRNA let-7g plays a crucial role in oxLDL-induced atherosclerosis, and which can bind to the 3'UTR region of LOX-1, inhibit the oxLDL-induced LOX-1/$[Ca^{2+}]_i$/PKC/OCT-1 signal transduction pathway, and reduce the oxLDL-mediated cell proliferation and migration. Hence, microRNA let-7g, modified let-7g, as well as their analogues of the present invention is sufficient to apply to pharmaceutical industry, being an active substance of medication for atherosclerosis so as to block the pathogenesis of atherosclerosis and to reduce the clinical symptoms. MicroRNA let-7g, modified let-7g, and their analogue in the present invention can be given to patients individually or combined with any acceptable excipients, carriers or other ingredients, and which can be manufactured into any form of medication, for example, pill, capsule, powder, solution and pastil, for easy and convenient delivery to patients.

Also, based on the feedback relationship between microRNA let-7g, transcription factor OCT-1, oxLDL and receptor LOX-1, microRNA let-7g of the present invention can be used as a diagnostic marker in clinical diagnosis of atherosclerosis. Due to the inhibitory effect of oxLDL on let-7g via the LOX-1/$[Ca^{2+}]_i$/PKC/OCT-1 pathway, the levels of let-7g in HASMCs will clearly be decreased.

Figure 35:
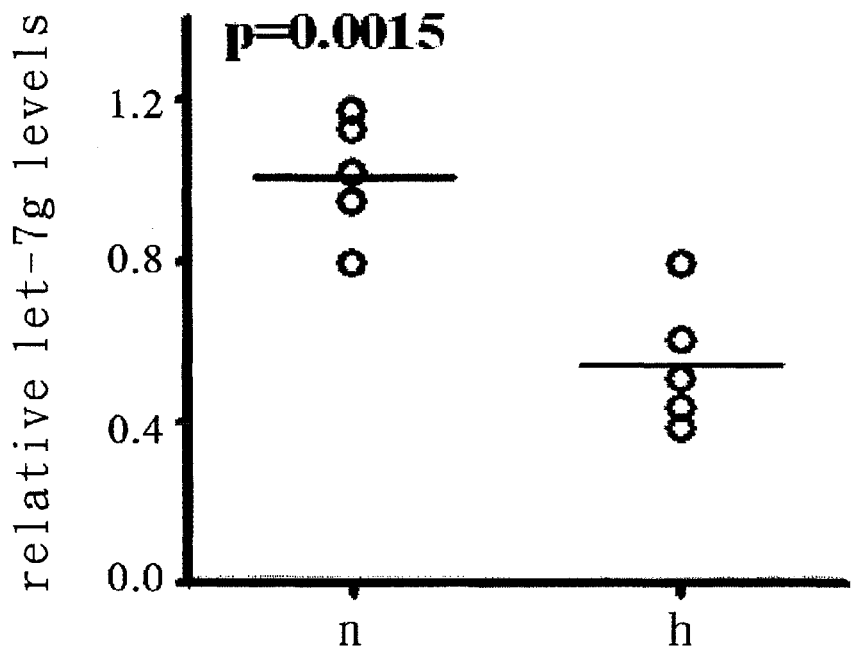
FIG. 35 is a diagram illustrating relative let-7g levels in mice.

In FIG. 35, the diagnostic function of let-7g is demonstrated in an animal trial. In the present embodiment, specific-pathogen-free mice-057BL/6J purchased from National Laboratory Animal Center in Taiwan, are prepared and divided into two groups, including (n), as a control; and (h), wherein the mice of group (n) has chow diet and the mice in group (h) has high-fat for six weeks. Then, total RNAs of groups (n) and (h) are collected and analyzed by real time PCR for determining the levels of let-7g in mice. In the present embodiment, a primer pair of mice let-7g is designed and used, and which is set forth in SEQ ID NO. 21 and 22.

As shown in FIG. 35, mice fed with high fat diet has significantly lower levels of let-7g as compare to mice fed with chow diet, and therefore, let-7g is adequate for being a diagnostic marker of hypercholesterol-related atherosclerosis.

Accordingly, a method of diagnosis of atherosclerosis can also be provided in the present invention, by identifying people at high risk of atherosclerosis according to the levels of let-7g in serum or plasma samples, as compare to individuals without atherosclerosis. Generally, the levels of let-7g in serum or plasma samples are determined by northern blotting assay, miRNA microarray and quantitative real time PCR. It is suggested people with lower levels of let-7g as comparing to individual free from atherosclerosis are incident to atherosclerosis and other relative cardiovascular diseases. With the determination of let-7g, a clinical diagnosis of atherosclerosis can be rapidly and specifically achieved so as to facilitate the clinical treatment of atherosclerotic patients.

With reference to TABLE 8, the diagnostic function of let-7g is further demonstrated in human samples. In the present embodiment, serum samples in any age and gender are collected and sorted to several groups by cholesterol level and history, including groups of (C), having 14 samples free from hypercholesterolemia (i.e. total cholesterol >240 mg/dl) and stroke; (T), having 15 samples, with total cholesterol >240 mg/dl but free from stroke; (S), having 16 samples of total cholesterol <240 mg/dl and stroke; and (ST), having 8 samples of cholesterol >240 mg/dl and stroke. Total RNAs of each serum sample are collected and analyzed by real time PCR for determining the levels of let-7g. In the present embodiment, the primer pair set forth in SEQ ID NO. 7 and 8 are selected and used to carry out the PCR analysis. Finally, data obtained from the PCR analysis is further computed and recorded in TABLE 8.

In TABLE 8, the $2^{-\Delta Ct}$ is obtained by $2^{-(TCt-ICt)}$, wherein the "TCt" is a Ct value (threshold/cycles of PCR) in the real time PCR of the present invention, and the ICt is the value of an internal control. In the present embodiment, the internal control is microRNA 16.

TABLE 8

Relative Levels of let-7g in serum samples

| Samples | Total cholesterol (TC) | Triglyceride (T; mg/dL) | $2^{-\Delta Ct}$ |
|---|---|---|---|
| C1 | 219 | 91 | 0.027593 |
| C2 | 212 | 51 | 0.023709 |
| C3 | 145 | 144 | 0.021292 |
| C4 | 186 | 72 | 0.019912 |
| C5 | 193 | 72 | 0.016253 |
| C6 | 200 | 56 | 0.076774 |
| C7 | 172 | 30 | 0.020541 |
| C8 | 139 | 57 | 0.028587 |
| C9 | 172 | 57 | 0.027879 |
| C10 | 214 | 63 | 0.028617 |
| C11 | 181 | 55 | 0.035359 |
| C12 | 180 | 68 | 0.038398 |
| C13 | 157 | 73 | 0.048939 |
| C14 | 161 | 122 | 0.056347 |
| T1 | 295 | 110 | 0.002973 |
| T2 | 252 | 490 | 0.003153 |
| T3 | 256 | 405 | 0.007778 |
| T4 | 261 | 95 | 0.012422 |
| T5 | 317 | 137 | 0.011874 |
| T6 | 241 | 53 | 0.029511 |
| T7 | 262 | 79 | 0.049549 |
| T8 | 248 | 92 | 0.024426 |
| T9 | 255 | 205 | 0.034343 |
| T10 | 254 | 79 | 0.01762 |
| T11 | 268 | 80 | 0.026284 |
| T12 | 347 | 44 | 0.021555 |
| T13 | 270 | 293 | 0.033999 |
| T14 | 264 | 76 | 0.024805 |
| T15 | 317 | 140 | 0.01936 |
| S1 | 158 | 61 | 0.012427 |
| S2 | 183 | 61 | 0.005545 |
| S3 | 157 | 66 | 0.007015 |
| S4 | 143 | 53 | 0.03774 |
| S5 | 188 | 44 | 0.064249 |
| S6 | 170 | 158 | 0.023707 |
| S7 | 189 | 170 | 0.02881 |
| S8 | 151 | 113 | 0.023077 |
| S9 | 101 | 59 | 0.028708 |
| S10 | 214 | 194 | 0.093935 |
| S11 | 135 | 77 | 0.042555 |
| S12 | 157 | 64 | 0.053315 |
| S13 | 147 | 96 | 0.014621 |
| S14 | 112 | 43 | 0.025887 |
| S15 | 152 | 93 | 0.029237 |
| S16 | 231 | 136 | 0.136139 |
| ST1 | 304 | 125 | 0.010187 |
| ST2 | 246 | 108 | 0.002053 |
| ST3 | 306 | 250 | 0.010299 |
| ST4 | 250 | 106 | 0.009068 |
| ST5 | 248 | 233 | 0.009633 |
| ST6 | 255 | 278 | 0.034558 |
| ST7 | 328 | 51 | 0.007639 |
| ST8 | 276 | 139 | 0.008045 |

Figure 36:
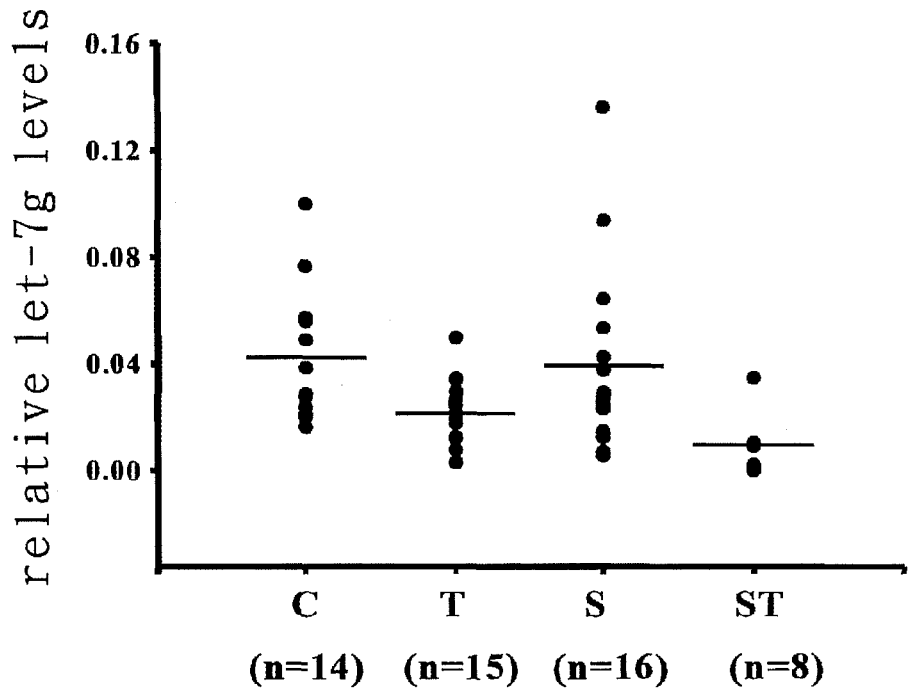
FIG. 36 is a diagram illustrating relative let-7g levels in clinical samples.

TABLE 8 and FIG. 36 show that hyper-cholesterol samples, such as groups (T) and (ST), have lower levels of let-7g than that of normal samples (C). Also, in compare with groups (ST) and (S), only the hyper-cholesterol related stroke samples have lower levels of let-7g. It is validated that, microRNA let-7g is sufficient to serve as a diagnostic marker in clinical diagnosis of atherosclerosis. By determining let-7g levels in serum samples, people at high risk to atherosclerosis, particular to hypercholesterol-related atherosclerosis, can be easily and specifically noticed, so as to facilitate the identification and clinical treatment of atherosclerotic subjects.

In summary, the method of diagnosis and therapy of atherosclerosis in the present invention provides a new strategy in clinical therapy and diagnosis of atherosclerosis, and not only can meet the need of rapid, sensitive and specific diagnostic assay of atherosclerosis, but also can effectively block the pathogenesis of atherosclerosis and prevent from serious cardiovascular diseases by administrating let-7, modified let-7g or their analogues. Hence, according to the present invention, the quality of clinical diagnosis and therapy of atherosclerosis will be significantly improved.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A method of preventing lectin-like oxidized low density lipoprotein receptor-1 (LOX-1) from entering vascular smooth muscle cells and endothelial cells, by providing microRNA let-7g, an analogue of let-7g or modified let-7g to organisms to inhibit the expression of lectin-like oxidized low density lipoprotein receptor-1, as well as the binding of lectin-like oxidized low density lipoprotein receptor-1 and oxidized low-density lipoprotein (oxLDL).

* * * * *